United States Patent [19]

Smith et al.

[11] Patent Number: 5,549,908
[45] Date of Patent: Aug. 27, 1996

[54] HYDROLYTICALLY LABILE MICROSPHERES OF POLYSACCHARIDE CROSSLINKED WITH CYANOGEN HALIDE AND THEIR APPLICATION IN WOUND DRESSINGS

[75] Inventors: Daniel J. Smith, Stow; Debashish Chakravarthy, Kent, both of Ohio

[73] Assignee: The University of Akron, Akron, Ohio

[21] Appl. No.: 65,742

[22] Filed: May 20, 1993

[51] Int. Cl.$^6$ ................................................ A61L 15/16
[52] U.S. Cl. ........................... 424/444; 424/445; 424/499
[58] Field of Search ................................. 424/445, 444, 424/499

[56] References Cited

U.S. PATENT DOCUMENTS

| | | | |
|---|---|---|---|
| 3,634,354 | 1/1972 | Andreassen | 260/252 |
| 3,914,183 | 10/1975 | Johansson et al. | 252/184 |
| 3,972,328 | 8/1976 | Chen . | |
| 4,253,460 | 3/1981 | Chen et al. . | |
| 4,538,603 | 3/1985 | Pawelchak et al. . | |
| 4,713,249 | 12/1987 | Schröder . | |
| 4,822,535 | 6/1980 | Ekman | 264/4.3 |
| 4,855,416 | 8/1989 | Usher . | |

FOREIGN PATENT DOCUMENTS

| | | |
|---|---|---|
| 47021405 | 11/1968 | Japan . |
| 1013585 | 12/1965 | United Kingdom . |
| 8809163 | 12/1988 | WIPO . |

OTHER PUBLICATIONS

Wang, Paul, Material Res. Soc. Sympos. Proc. (1988) Volume Date 1987, 110 (Biomed. Mater. Deviles), 377–86. (Abstract).
Axen et al., European J. Biochem. 18 (1971) 351–360.
Kagedal et al., Acta Chemica Scandinavia 25 (1971) 1855–1859.

*Primary Examiner*—Nathan M. Nutter
*Assistant Examiner*—Richard Jones
*Attorney, Agent, or Firm*—Renner, Kenner, Greive, Bobak, Taylor & Weber

[57] ABSTRACT

A water swellable and hydrolytically labile (and therefore potentially biodegradable) non-toxic crosslinked polysaccharide in microsphere or bead form. The crosslinked polysaccharide comprises polysaccharide chains and crosslinking groups which are imidocarbonate groups, carbonate groups or a mixture thereof. The microspheres are predominantly in the range of about 1 micron to about 100 microns in diameter, preferably about 2–50 microns. The crosslinked polysaccharide polymer, which is preferably a crosslinked dextran, is formed by treating a water soluble non-crosslinked polysaccharide with a cyanogen halide (preferably cyanogen bromide) in an aqueous alkaline medium which is the disperse phase of a water-in-oil dispersion. The microspheres are useful in the treatment of wounds, in particular as an absorptive agent for wound exudates. The microspheres may be formed into a wound dressing which includes a blend of the microspheres and a hydrophobic adhesive matrix material on a waterproof backing sheet.

26 Claims, 4 Drawing Sheets

HYDROLYTICALLY LABILE MICROSPHERES OF POLYSACCHARIDE CROSSLINKED WITH CYANOGEN HALIDE AND THEIR APPLICATION IN WOUND DRESSINGS

TECHNICAL FIELD

This invention relates to wound dressings of the hydrocolloid type and to absorptive materials therefor. More particularly, this invention relates to a novel hydrolytically degradable absorptive agent in bead or micro sphere form and to its use in wound dressings, particularly hydrocolloid (HCD) dressings.

BACKGROUND ART

Various classes of dressings are currently used in the management of acute and chronic dermal wounds. Of these, the hydrocolloid dressings (HCD) dressings are used most frequently in the clinical setting. The high absorptive capacity characteristic of these dressings coupled with the occlusive and moist environment they provide lead to rapid granulation, re-epithelialization and wound closure.

Clinical applications for HCD dressings include the treatment of burns and burn donor sites, chronic venous ulcers, decubitus ulcers, leprous ulcers, epidermolysis bullosa, scleroderma, psoriasis and non-infected partial thickness wounds.

Conventional HCD dressings incorporate an adhesive mixture, usually composed of low and high molecular weight polyisobutylene, and absorbents such as gelatin, pectin and carboxymethyl cellulose, silica and cotton fibers. Representative HCD dressings are described, for example, in U.S. Pat. Nos. 3,972,328 (Aug. 3, 1976) to Chen, et al, 4,253,460 (Mar. 3, 1981) to Chen, et al, and 4,538,603 (Sep. 3, 1985) to Pawelchak, et al.

Residual material components from HCD dressings have often been noted in the healing wound. In most cases, despite the presence of such extraneous substances, wounds re-epithelialize and close in the course of time, with no externally visible abnormalities. Recently reported histologic evaluations, however, of such apparently healed wounds in animals have indicated deep-seated foreign body type reactions and granulomata formations (Young, et al, *Journal of Investigative Dermatology*, vol. 97, pgs. 586–592, 1991). These effects have been attributed to the dressing residues that remain in the wound after healing and closure. The clinical relevance and the long-term implications of such deep-seated chronic inflammation is still unknown. However, the presence of inflammatory dressing residues can be expected to extend the inflammatory phase of wound healing and thus adversely affect the processes of granulation, matrix formation, tissue remodeling, re-epithelialization, and wound closure. Despite these recently raised questions, it is likely that HCD dressings will remain in widespread clinical use for the treatment of dermal wounds. Elimination of both acute and chronic foreign body-type reaction from HCD dressings is therefore a desirable goal.

Various absorbents are currently used in the formulation of wound fillers and dressings. The key feature of these absorbents in their choice as wound dressing components appears to be their fluid handling capacity; biodegradability has not been an issue of major concern. In view of this, it is not surprising that recent histological studies show that the use of certain wound dressings lead to extensive non-resolved and deepseated chronic inflammation in externally healed tissue. Such inflammation can potentially be reduced by using dressing components that degrade to non-toxic and non-inflammatory products under physiological conditions. In this context it should be noted that none of the commonly used biodegradable microspheres in controlled drug delivery (such as polylactides or gylcollides) possess any appreciable absorptive or fluid handling capacity.

Young, et al, cited supra describes a study which compares the effects of a semi-occlusive adhesive polyurethane dressing with a hydrocolloid dressing. The deep seated chronic inflammation noted with the hydrocolloid dressing was not observed with the semi-occlusive dressing. On the other hand, semi-occlusive dressings do not have the capacity to absorb wound exudate which is a key characteristic of hydrocolloid dressings.

Improvements in hydrocolloid dressing formulation is a desirable approach in order to eliminate both acute and chronic foreign body-type reactions of presently known hydrocolloid dressings while preserving the capacity to absorb exudate which is also characteristic of hydrocolloid dressings. In particular, a hydrocolloid dressing component which is both absorptive and biodegradable is needed.

SUMMARY OF THE INVENTION

This invention according to one aspect provides a novel polymer composition which is both absorptive and hydrolytically degradable.

The novel polymer composition of this invention is a water swellable, water insoluble, hydrolytically labile and pharmaceutically acceptable crosslinked polysaccharide (preferably dextran) polymer composition in the form of beads or microparticles. The microparticles are essentially spherical in shape and so may be referred to as microspheres. The product when dry is a free-flowing powder. The crosslinking groups are linear imidocarbonate groups, linear carbonate groups or a mixture thereof. Products of this invention are water insoluble at 25° C. and are degradable to a water soluble non-crosslinked polysaccharide in an essentially neutral aqueous medium at a temperature of at least 37° C. Because the products of this invention are degradable in essentially neutral aqueous media, they may be characterized as hydrolytically labile (or hydrolytically degradable). Hydrolytic lability also indicates that the products of this invention are biodegradable, i.e., capable of decomposition into water soluble products in the presence of aqueous body fluids such as blood and lymph at normal body temperature (37° C.).

Microspheres of this invention are formed by crosslinking of a water-soluble non-crosslinked polysaccharide with a cyanogen halide under alkaline conditions under which crosslinking occurs, in the aqueous phase of a water-in-oil dispersion. The preferred cyanogen halide is cyanogen bromide. The crosslinked product of this invention comprises polysaccharide chains and crosslinking groups formed by the aforesaid reaction with cyanogen halide and base. The crosslinking groups as formed are believed to be linear imidocarbonate groups which are bonded to different polysaccharide chains (or to distant parts of the same chain) through hydroxyl groups on the polysaccharide chains. These linear imidocarbonate groups may be partially hydrolyzed in acid to linear carbonate groups during workup.

The crosslinked product is essentially free of crosslinking groups other than those introduced through reaction with cyanogen halide and base. In particular, the crosslinked product is free of non-hydrolytically degradable crosslinking groups.

The starting polysaccharide is water soluble and may have a molecular weight from about 40,000 to about 1,000,000 or more. Preferably the starting polysaccharide has a molecular weight (average) from about 100,000 to about 1,000,000, more preferably from about 200,000 to about 600,000. The preferred starting polysaccharide is dextran.

The microparticles of this invention are essentially spherical in shape and are predominantly in the range of about 1 to about 100 microns. Generally the microparticles are predominantly in the range of about 2 to about 50 microns in diameter. The final product microspheres are in the form of a free-flowing powder.

It is essential to carry out the activation reaction in the aqueous phase of a water-in-oil dispersion in order to obtain spherical microparticles in the size ranges defined above. If water (without any oil phase) is used as the reaction medium a gel is initially formed. This gel must be broken up (e.g., in a blender) in the present of a dehydrating solvent such as ethanol in order to obtain a useful product. The final product of such processing is not in the form of spheres but rather is in the form of irregularly shaped aggregates.

Products of this invention, being in the form of microspheres, offer several advantages over products in the form of aggregates. First, processing and formulation are easier. Second, the product is more uniform. As a consequence, products of this invention exhibit more uniform and more predictable degrees of swelling, rates of swelling and rates of hydrolysis or degradation in the presence of moisture than would a product in the form of aggregates.

This invention according to another aspect provides a process for producing the aforesaid crosslinked polysaccharide composition in the form of microspheres. This process comprises:

a) forming an aqueous alkaline solution of a water soluble non-crosslinked polysaccharide;

b) forming a water-in-oil dispersion comprising said aqueous alkaline solution and a water immiscible organic liquid;

c) treating the dispersion with a cyanogen halide; and d) recovering microspheres of a water swellable, water insoluble, hydrolytically labile crosslinked polysaccharide.

The preferred cyanogen halide is cyanogen bromide.

This invention according to still another aspect provides an adhesive composition for a wound dressing. This composition comprises a minor amount of water swellable and hydrolytically labile crosslinked polysaccharide microspheres as above described, dispersed in a major amount of an adhesive and pharmaceutically acceptable amorphous hydrophilic polymeric matrix material.

BRIEF DESCRIPTION OF THE DRAWINGS

In the drawings:

FIGS. 1–8 all show swelling and degradation (i.e., bead volume as a function of time) of beads prepared according to this invention and immersed in an aqueous medium at an elevated temperatures (either 38° C. or 60° C.) as more fully set forth in the examples.

DESCRIPTION OF THE PREFERRED EMBODIMENTS

Figure 1:
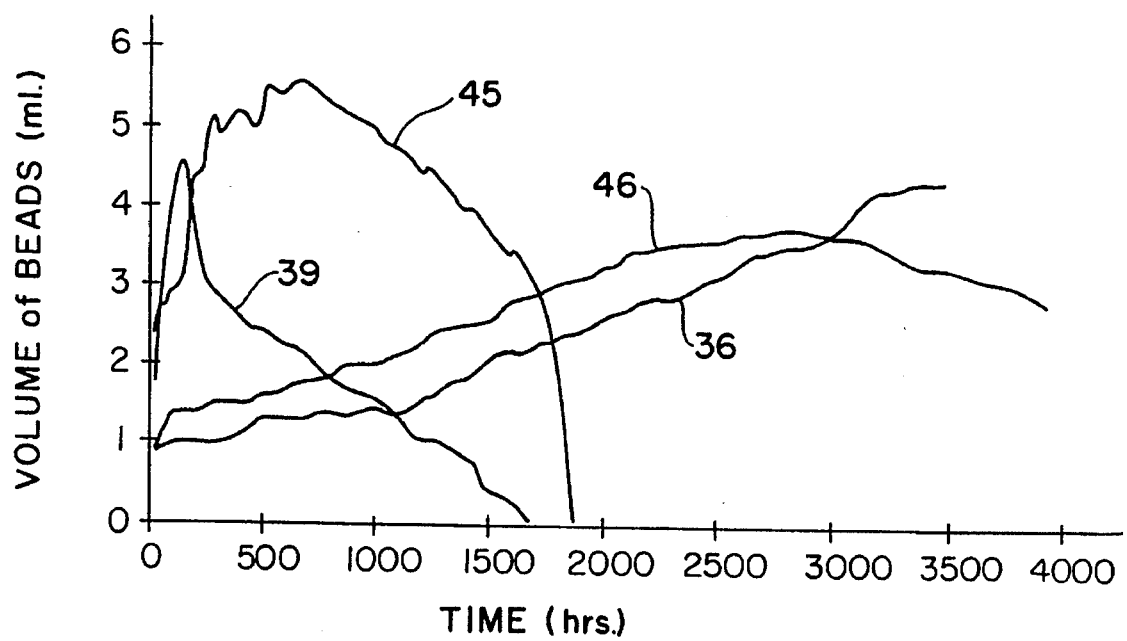
FIG. 1 is a graphical representation of the data in Table III-A.

The starting polysaccharide is a water soluble non-crosslinked polysaccharide. The molecular weight of the starting polysaccharide may be from about 40,000 to about 1,000,000 or even higher (say up to about 2,000,000). The starting polysaccharide preferably has on average molecular weight from 100,000 to about 1,000,000, more preferably from about 200,000 to about 600,000. The starting polysaccharide may be either essentially linear or branched, but is not crosslinked to render it insoluble. In particular, the starting polysaccharide must be free of crosslinking groups, such as the hydroxypropyl ether group derived from epicholorohydrin for example, which is not hydrolytically degradable and hence not biodegradable.

The preferred starting polysaccharide is dextran. The dextran has an average molecular weight from about 40,000 to about 1,000,000 or higher (say 2,000,000), preferably about 100,000 to about 1,000,000, more preferably about 200,000 to about 600,000.

Water insoluble polysaccharides, whether crosslinked or not, are not suitable starting materials. By way of example agarose, which is water insoluble whether or not crosslinked, is not suitable as a starting material.

The non-crosslinked polysaccharide is crosslinked with a cyanogen halide, preferably cyanogen bromide, CNBr, in a strongly alkaline aqueous medium. The aqueous medium is made alkaline with a strong base such as sodium hydroxide. The alkaline aqueous medium is the aqueous phase of a water-in-oil dispersion. A water immiscible inert organic liquid constitutes the organic or oil phase.

The amount of cyanogen halide (which is preferably cyanogen bromide) is from about 0.01 to about 0.25 moles per mole of polysaccharide hydroxyl groups present. The amount of cyanogen halide added affects the crosslinking density. The cyanogen halide is preferably dissolved in water and added as an aqueous solution to the polysaccharide solution.

A range of products having different degrees of water swellability and different rates of degradation (or redissolution) in aqueous media at elevated temperature of 37° C. and above. Both the degree of water swellability and the redissolution rate in aqueous media decrease as the crosslinking density increases. Redissolution rate also decreases with increasing average molecular weight of the starting polysaccharide.

The starting non-crosslinked polysaccharide (e.g., dextran) is dissolved in water. This can be done at ambient temperature. The concentration of polysaccharide in the aqueous solution can be varied over a wide range. The polysaccharide concentration (prior to the addition of cyanogen bromide) may vary from about 10% by weight of polysaccharide up to the limit of solubility of the polysaccharide. Typically the polysaccharide concentration is from about 15–50% by weight of polysaccharide, the balance being essentially water. Higher polysaccharide concentrations, e.g., about 25% by weight, are preferred, at lower crosslinking densities, especially when lower starting polysaccharide molecular weights are used, since the desired microspheres do not form when both lower concentrations of polysaccharide and lower crosslinking densities are used.

A strong base, such as sodium hydroxide is added to the polysaccharide solution. A strong base, such as sodium hydroxide or potassium hydroxide, is used instead of a more weakly basic material, such as sodium carbonate or triethylamine, as the alkaline material. The quantity of sodium hydroxide added is substantially equivalent to the quantity of cyanogen bromide to be added subsequently. A slight excess of sodium hydroxide or other strong base may be used, but a large excess should be avoided since cyanogen bromide (or other halide) will simply react with the excess strong base instead of reacting with hydroxyl groups of the polysaccharide to form crosslinking groups. The resulting alkaline solution of polysaccharide is strongly basic, having a pH from about 13 to about 14. Quantities of both alkali metal hydroxide and cyanogen bromide should be at least about 0.08 mole per liter of water forming the aqueous phase, preferably from about 0.08 to about 0.8 mole per liter of water, in order to form microspheres. Microspheres do not form at more dilute concentrations. In the range actually studied, as shown in the examples, microspheres were obtained when the sodium hydroxide concentration range was from about 0.09 to about 0.6 moles per liter of water of solution (including water in which the CNBr was dissolved as well as in which dextran was dissolved). At lower alkali and cyanogen bromide concentrations, microspheres did not form.

A water-in-oil dispersion in which the alkaline polysaccharide solution is the aqueous phase is formed by mixing the aqueous solution with a large volume of an inert water immiscible organic liquid. A light mineral oil was actually used, but other inert water immiscible organic liquids having similar viscosity can be used as desired. A dispersion is maintained by strong agitation. It is not necessary to use a surfactant.

A cyanogen halide, preferably cyanogen bromide, is added to the alkaline water-in-oil dispersion while vigorous stirring is continued. This compound is preferably water soluble since crosslinking takes place in the aqueous phase. The cyano compound must be at least partially water soluble. The amount of cyanogen bromide added, which can be expressed either in terms of moles of CNBr per mole of polysaccharide hydroxyl groups (specifically dextran hydroxyl groups, denoted "dextran-OH" herein) or in terms of weight of cyanogen bromide per unit weight of dextran (or other polysaccharide), can be varied in accordance with the desired crosslinking density in the final product. Examples herein illustrate a twenty-fold difference in CNBr/dextran-OH mole ratio, and either higher or lower ratios than those actually shown in the examples can be used. The examples illustrate CNBr/dextran-OH mole ratios from about 0.01 moles up to about 0.2 (actually 0.21) moles of CNBr per mole of dextran hydroxyl groups. The CNBr/dextran-OH mole ratio is a convenient measure of the crosslinking density of the product, whether or not all of the CNBr actually forms crosslinking groups. (The course of reaction will be discussed in further detail below.)

The number of moles of dextran-OH groups is equal to the weight of dextran activated divided by 54. This value of 54 is obtained by dividing the formula weight of a repeating unit in dextran (which is 162) by the number of free hydroxyl groups (3) in each repeating unit. (Dextran is composed of repeating glucopyranose units; the formula weight of these repeating units is 162.)

The cyanogen bromide may be added in aqueous solution as a matter of convenience. Concentration of the cyanogen bromide solution has a slight but not profound effect on the outcome, as will be more apparent from the examples.

Cyanogen bromide is the preferred crosslinking agent, although other cyanogen halides can be used. Cyanogen iodide has been reported in the literature as an activating agent, but is much slower to react, and is therefore not as desirable as cyanogen bromide. Also, cyanogen bromide is water soluble while cyanogen iodide and cyanogen chloride are only slightly soluble in water. Other cyano compounds have been reported in the literature as activating agents for polysaccharides (although most of the literature is directed toward cyanogen bromide). An activating agent for the present invention must be electrophilic and at least partially water soluble, so that it will enter the aqueous phase and not the oil phase of the dispersion.

The quantities of cyanogen bromide (or other cyanogen halide) and alkali metal hydroxide should be substantially equimolar; however, a slight excess of alkali metal hydroxide can be used. Excellent results are obtained with a 5–6% excess of sodium hydroxide, as illustrated in the examples herein. A deficiency of alkali metal hydroxide will result in incomplete crosslinking and failure to utilize all CNBr. It has been found that large excesses of alkali metal hydroxide result in failure to form the desired crosslinked product.

Crosslinking in an aqueous water-in-oil dispersion is very important so that the crosslinked polysaccharide product will be in the form of microparticles, which are typically essentially spherical and which can therefore be called microspheres. These microparticles as produced and after drying are of size as stated above.

The final product will be in the form of discrete microspheres of crosslinked polysaccharide are obtained under most possible combinations of polysaccharide concentration, crosslinking density (measured by CNBr/dextran-OH mole ratio) and polysaccharide molecular weight discussed above. The desired microspheres have been found to form consistently when the CNBr/dextran-OH mole ratio is at least about 0.04. At lower CNBr/dextran-OH mole ratios, e.g., 0.01 or 0.02, the concentration of polysaccharide in aqueous solution should be increased in order to assure the formation of the desired microspheres, since these low crosslinking densities and concomitant low alkali and cyanogen bromide concentrations in combination with low concentration of polysaccharide appear to result in failure to form the desired microspheres. This will be illustrated and explained further in the examples.

Microspheres were formed over the entire range of crosslinking densities studied, from about 0.01 up, in Example VIII, wherein relatively concentrated solutions were used at low crosslinking densities. On the other hand, when more dilute solutions and smaller batch sizes were used, as illustrated in Example I and Comparative Example A, crosslinking of a high molecular weight dextran (average M.W. 515,000) at a crosslinking density of 0.021 yielded crosslinked products which agglomerated and did not yield microspheres on workup and drying (batches 38 and 39 in Example I), and reaction of a low molecular dextran (average M.W. 40,000) did not yield a water insoluble product, indicating that crosslinking did not take place.

Reaction herein is believed to proceed in fashion analogous to that described in Kohn, et al, *Analytical Biochem-* istry, vol. 115, pages 375–382 (1981) except that (1) there will be no hydrolytically stable (i.e., non-labile) crosslinking groups present in the product since none are present in the starting material herein; (2) the reaction herein is carried out in the aqueous phase of a water-in-oil dispersion, resulting in formation of microspheres; (3) sodium hydroxide (or other alkali metal hydroxide) is used as the alkaline material instead of potassium carbonate, $K_2CO_3$, and (4) quantities of NaOH and CNBr are essentially stoichiometric. Of the various possible reaction products given in Kohn, et al, (i.e., cyanate, carbamate, linear imidocarbonate, and cyclic imidocarbonate), it is believed that both linear imidocarbonate and cyclic imidocarbonate are the reaction products formed herein; that little if any carbamate is formed; and that any cyanate formed is merely an intermediate which is transformed into an imidocarbonate as shown in Kohn, et al. Formation of a water insoluble product upon reaction with cyanogen bromide furnishes evidence that linear imidocarbonate crosslinking groups are formed, without ruling out possible formation of the other groups listed above, all of which are non-crosslinking.

Reaction takes place very quickly. Continued agitation is necessary for only about 30 seconds to 2 minutes after addition of cyanogen bromide is complete. The reaction mixture is then allowed to settle. The organic phase is diluted with a solvent such as hexane or petroleum ether, and then removed e.g., by decantation from the mixing vessel. The aqueous phase can be washed with further quantities of water immiscible organic solvent such as petroleum ether to effect complete removal of mineral oil.

The crosslinked product as formed is a water insoluble translucent hydrated aggregation of microspheres. It comprises polysaccharide chains and linear imidocarbonate groups, and may therefore be represented by the formula (I) following. It exhibits an alkaline reaction. As previously indicated, the product may also comprise cyclic imidocarbonate groups.

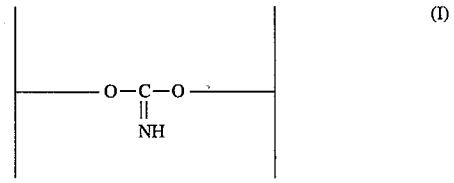

(I)

As reported in the literature, linear imidocarbonate groups are formed by reaction of CNBr with two dextran (or other polysaccharide) hydroxyl groups on different polysaccharide chains. (Some linear imidocarbonate groups may link distant regions of the same polysaccharide chain; these groups will be essentially linear.) Also as reported in the literature, cyclic imidocarbonate groups are formed by reaction of CNBr with two dextran (or other polysaccharide) hydroxyl groups on the same polysaccharide chain, forming a 5-member ring in the case of dextran. Both linear and cyclic imidocarbonate groups are formed by reaction of one mole of CNBr with two moles of dextran hydroxyl groups. Thus, crosslinking of dextran at a crosslinking density (or CNBr/dextran-OH mole ratio) of 0.25 involves reaction of a total of 0.5 moles of free hydroxyl groups in the polysaccharide chains (theoretically, assuming no hydrolysis).

Cyanogen bromide is toxic; therefore, appropriate precautions should be taken to avoid escape of vapors, e.g., use of a hood on laboratory scale, and a fluid tight reaction vessel and exit conduit on larger scale.

The product as formed (which may be called an intermediate) may be converted to the desired final product by a workup procedure which may include acidification followed by neutralization. The microparticles or beads of the crosslinked polysaccharide as formed are dispersed in water or a hydrophilic organic solvent such as 95% ethanol. The suspension may then be acidified with a strong or moderately weak non-toxic acid to a pH not greater than about 3. The suspension is preferably acidified with a strong mineral acid, such as hydrochloric acid (preferred) or sulfuric acid to a pH between about 2 and about 3. However, other non-toxic acids such as acetic acid can be used. Acidification may be followed by gentle heating for a brief time, e.g., at 40° C. for 30 minutes (more broadly, from about 35° C. to about 50° C. for about 10 minutes to one hour).

Acidification converts any cyanide present to hydrogen cyanide and heating aids the escape of any vapors so formed. (This requires appropriate precautions to prevent escape of any reaction vapors, e.g., a hood on laboratory scale, and a fluid tight reaction vessel and exit conduit on larger scale, since hydrogen cyanide is toxic). Actually, no cyanide is present on the final product surfaces, without heating and even without acidification, as shown by Examples III and IV. Heating can therefore be omitted if desired. While acidification to a low pH (about 2 to 3) is not necessary for cyanide removal, it is desirable to add enough acid to neutralize the product, which is quite alkaline as formed, to a pH of about 7 (e.g., about 6.5–7.5) for pharmaceutical acceptability. Absence of cyanide in the finished beads indicates that (1) CNBr reacts only with polysaccharide hydroxyl groups and that there is minimal if any reaction of CNBr with NaOH, and (2) the workup methods described herein are all adequate to remove free cyanide ion from the finished product.

Acidification may cause chemical modification of the activated crosslinked product, although the exact nature and extent of this modification has not been determined. Some nitrogenous species remain, since nitrogen is found in the final product. However, it is possible, even probable, that some modification takes place as a result of acid hydrolysis, based on the teachings of Kohn, et al, *Analytical Biochemistry*, vol. 115, pages 375–382 (1982) at pages 376–378. It is believed that at least a portion of the linear imidocarbonate groups remain as such, although possibly a portion of the imidocarbonate groups are converted to linear carbonate groups, giving a crosslinked polymer which is partially of the formula (II) below.

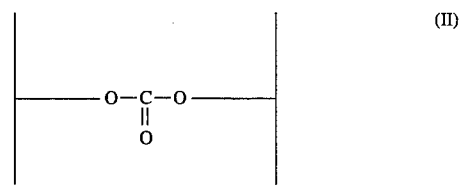

(II)

The product after acidification comprises polysaccharide chains and crosslinking groups selected from the group consisting of linear imidocarbonate crosslinking groups, linear carbonate crosslinking groups, and mixtures thereof. Additional groups, e.g., carbamate groups and cyclic imidocarbonate groups or acid hydrolysis products thereof, may be present. Although the exact chemical nature of the product has not been ascertained, the inventors have been able to reproduce the results and obtain final products having desired characteristics, as will be described below.

After acidification, the crosslinked polysaccharide is neutralized to approximately neutral pH, e.g., about 6–8 and more particularly about 6.5 to about 7.5, using a non-toxic base such as sodium hydroxide (preferred), potassium hydroxide or sodium carbonate. The product may then be dehydrated and/or dried by means known in the art, as for example (preferably) by successive treatment with solvents capable of removing water, e.g., 95% alcohol followed by either absolute ethanol or acetone. The product can be dried under conventional drying conditions, e.g., air drying at ambient temperature or by freeze drying. If desired, one may first treat with dehydrating solvents and then finish by oven drying at about 100°–125° C. It is believed that no further chemical reaction takes place during neutralization and washing.

Alternatively, the product as formed from the crosslinking procedure may be neutralized directly to an essentially neutral pH (about 6.5 to about 7.5), using sufficient non-toxic acid (e.g., HCl) for this purpose. (The product as formed is strongly alkaline.) It has been found that acidification is not necessary since cyanide is not present in the final product in either case. The final product is believed to contain a greater percentage of imidocarbonate and a correspondingly smaller percentage of carbonate whether the product is neutralized but not acidified.

The final product is a water insoluble hydrolytically degradable amorphous material in the form of beads or microparticles which are essentially spherical and which have particle diameters in the range of about 1 micron to about 100 microns, and typically from about 2 microns to about 50 microns. Chemically the final product comprises polysaccharide chains and hydrolytically labile crosslinking groups which are believed to be a mixture of linear imidocarbonate groups and linear carbonate groups. That is, the structure of the final product is believed to be a mixture of products of the formula (I) and formula (II). Such product may contain, (although does not necessarily contain) additional non-crosslinking groups (not shown in formulas I or II), as for example carbamate, or cyclic imidocarbonate and/or hydrolysis products thereof, as mentioned earlier.

The final products of this invention comprise polysaccharide chains and crosslinking groups selected from the group consisting of linear imidocarbonate groups, linear carbonate groups, and mixtures thereof.

Microparticles of crosslinked polysaccharides according to the present invention are water insoluble at ambient temperature (about 20° C.–25° C.). However, these microparticles swell in aqueous media as described more fully in the examples. Greater degrees of swelling are associated with lower degrees of crosslinking. Similarly, microparticles of crosslinked polysaccharides of this invention are swellable at wound sites, absorbing wound exudates. The less highly crosslinked and therefore more absorbent crosslinked polysaccharides are suitable for fresh wounds, which typically have substantial volumes of exudate. The more highly crosslinked and therefore less absorptive crosslinked polysaccharides of this invention are suitable in the treatment of mature wounds, where typically the volume of exudate is less.

The degree of swelling varies inversely with the degree of crosslinking. While the degree of crosslinking has not been measured (since the extent of formation of linear imidocarbonate groups vs. the extent of formation of other possible groups during activation has not been determined), the inventors have found results to be reproducible and find that the degree of swelling correlates inversely with the mole ratio of cyanogen bromide to dextran hydroxyl groups. This mole ratio can therefore be used as a measure of the degree of crosslinking. Swelling takes place in aqueous fluids over the entire temperature range from freezing to boiling, although it proceeds faster as temperature is increased.

The final products of this invention are also easily hydrolytically degradable. That is, they gradually revert to water soluble non-crosslinked polysaccharides in the presence of moisture. They are hydrolyzed to water soluble non-crosslinked polysaccharides in essentially neutral water or other essentially neutral aqueous media (including blood and lymph) at temperatures of 37° C. (normal human body temperature) and higher. This can be demonstrated in the laboratory by exposure of the product of the invention to water at an elevated temperature of 37° C. or higher (an accelerated degradation test at 60° C. being convenient for demonstration purposes.) The water soluble polysaccharide formed on hydrolysis or hydrolytic degradation has about the same chain length as the parent or starting non-crosslinked polysaccharide as far as is known. Hydrolysis to water soluble products in vitro indicates that a product of this invention will biodegrade under typical physiological condition. The result of hydrolytic degradation of crosslinked dextran beads is dextran; dextran is metabolized or excreted through well characterized means.

Biodegradability of absorbent components is very important in wound dressings. As a result of hydrolytic degradability, any microparticles of the present invention which get into a wound from a wound dressing will be gradually cleaved to non-toxic biodegradable products, e.g., dextran, so that no undissolved particles remain. Microparticles of this invention will not cause deep seated non-resolvable long term inflammation at a wound site as is the case with certain presently known wound dressings which contain non-biodegradable particulate ingredients.

Hydrolytic degradability of the products of this invention is a consequence of the fact that the only crosslinking groups present are those introduced during chemical activation and any hydrolysis products thereof, e.g., linear imidocarbonate, linear carbonate and mixtures thereof. These crosslinking groups are labile, i.e., they undergo hydrolytic scission under mild conditions, in particular, exposure to essentially neutral water or human body fluids (which are aqueous in nature) at temperatures of 37° C. or higher. In particular, no stable or non-biodegradable crosslinking groups, such as those derived from epichlorohydrin, are present.

The rate of aqueous degradation varies inversely with the degree of crosslinking. That is, a more highly crosslinked polysaccharide according to this invention degrades more slowly at any given temperature than does a less highly crosslinked polysaccharide.

The rate of hydrolytic degradation increases with temperature. Thus, for example, a given crosslinked polysaccharide product of this invention will degrade more rapidly at 60° C. (which is used for accelerated tests in the examples) than at 37° C.

The crosslinked polysaccharides of this invention are in contrast to cyanogen bromide-activated polysaccharides prepared from water insoluble polysaccharides such as dextran crosslinked with epichlorohydrin ("Sephadex"), or agarose ("Sepharose") or crosslinked agarose, all of which are known in the prior art. Prior art cyanogen bromide activated polysaccharides prepared from their parent water insoluble starting polysaccharides are not hydrolytically degradable (or biodegradable) under the conditions described herein. For example, "Sephadex" G-200 can withstand boiling phosphate buffer solution for 24 hours without any apparent degradation. ("Sephadex" is a registered trademark of Pharmacia Fine Chemicals AB of Uppsala, Sweden (distributed in the United States by Pharmacia, Inc., Bio-Technology Group, Piscataway, N.J.)). Where a stable crosslinking group such as the hydroxypropyl ether group from the use of epichlorohydrin is present, that group will remain, so that the crosslinked polymer is non-biodegradable by mammalian tissue. If the starting polysaccharide is water insoluble, as is the case with agarose, such polymer also will be non-biodegradable. An important requirement of the present invention is that the products of this invention must be prepared from a water soluble polysaccharide.

Crosslinked polysaccharide microspheres of this invention are especially advantageous as an absorptive component of wound dressings. A wound dressing according to this invention may comprise, for example, a blend of crosslinked polysaccharide microspheres of this invention with a hydrophobic adhesive polymeric matrix material, which blend is applied to one side or surface of an inert waterproof backing sheet.

The matrix material may be an amorphous polymer (having a glass transition temperature but no melting point) which is hydrophobic, chemically inert, pharmaceutically acceptable, adhesive, and solid at body temperatures. To the latter end, the glass transition temperature should be at least slightly above normal body temperature, e.g., not lower than about 45° C.

Suitable matrix materials are known in the art. The matrix material is rubbery (i.e., elastomeric) and hydrophobic. Examples of suitable matrix materials include various grades of polyisobutylene styrene-butadiene rubber, and butyl rubber (a copolymer of isobutylene with a small amount of isoprene). A low molecular weight polyisobutylene (average M.W. about 10,000 to about 50,000) is typically a matrix component. U.S. Pat. Nos. 3,972,328, 4,253,460 and 4,538,603, all cited supra, illustrate suitable matrix materials.

The quantity of polysaccharide microparticles according to the present invention must be sufficient to lend an effective degree of absorbtivity for water and aqueous body fluids (blood and lymph) to the blend or composition. This amount will be from about 2% to about 50% by weight of total blend weight. Preferably the amount of microparticles of this invention is from about 5 to about 30% by weight, more preferably from about 10% to about 25% by weight, particularly about 15% to about 20% by weight, of total blend weight.

Conversely, the matrix material constitutes the remainder of the blend or composition. Additional components (e.g., additional absorptive materials are not required. The amount of matrix material must be sufficient to lend adhesiveness and integrity to the composition, and is broadly from about 50% to about 98% of total blend weight, preferably from about 70% to about 95% of total blend weight, more preferably from about 75% to about 90%, most preferably from about 80% to about 85% of total blend weight.

The backing sheet may be a conventional bandage backing sheet. Such backing sheets are typically formed of water vapor permeable polyurethane.

Microspheres of derivatized dextrans, i.e., crosslinked polysaccharides which contain a derivative group which is different from and in addition to any group introduced by cyanogen halide treatment, and which contain crosslinking groups in accordance with this invention (i.e., imidocarbonate, carbonate or a mixture thereof), can also be prepared in accordance with this invention. Such microspheres can potentially be used as controlled drug delivery vehicles. A derivatized and crosslinked dextran prepared in accordance with this invention will typically release a pharmaceutically active material more slowly than will the corresponding derivatized dextran which is not crosslinked.

Two derivatized and crosslinked polysaccharides in the form of microspheres will be discussed for purposes of illustration.

Arginine grafted and crosslinked beads or microspheres can be prepared by a procedure such as that described in Example XII. Arginine is a model nucleophilie. Quantities of NaOH and CNBr are essentially stoichiometric. Other neucleophiles which are pharmaceutically active can be grafted onto dextran in a similar manner to produce a slow release drug delivery material in microsphere form.

Another application of the technique is to prepare microspheres of crosslinked dextran sulfate, wherein the crosslinking groups are imidocarbonate groups, carbonate groups or a mixture of the two. Microspheres of crosslinked dextran sulfate may be used for controlled drug delivery to tissue.

Crosslinked dextran sulfate microspheres can be prepared by either of two procedures: (1) sulfation of a starting non-crosslinked dextran (or other non-crosslinked water soluble polysaccharide) by means known in the art followed by crosslinking with CNBr and alkali (e.g., NaOH), or (2) crosslinking a water soluble dextran with CNBr and alkali (e.g., NaOH) according to this invention and is described above, and then sulfating, which may be done by means known in the art. The first is preferred and is illustrated in the examples. It will be noted that the quantity of NaOH required in the preferred first method is in excess of the stoichiometric quantity based on the amount of CNBr reacted.

EXAMPLES

This invention will now be described in further detail with reference to the examples which follow.

Example I

Starting Materials

Dextran (non-crosslinked and water soluble) of 40,000 and 515,000 (nominal 500,000) average molecular weight were obtained from Sigma Corporation, St. Louis, Mo., U.S.A. These were produced by Leuconostoc mesenteroids, Strain Na B-512.

Other reagents and solvents are given in the description which follows.

Preparation of the Microspheres

Three series of microspheres, designated A, B, and C, were prepared by varying the proportions of the reactive species, i.e., dextran, cyanogen bromide and NaOH, as shown in Tables I-A, I-B and I-C. Typically, 3.6 gms of dextran was dissolved in 15.6 ml of water, followed by the addition of 10M NaOH. The solution was then poured into a Waring blender (Waring Commercial Blender, Model H68-100, 33BL50; Waring Products Division, Dynamics Corporation of America, West Hartford, Conn., U.S.A.) containing 300 ml of light mineral oil. The mixture was stirred at high speed. Cyanogen bromide, dissolved in water, was added to the mixture in the blender. After 2 minutes of further stirring, the mineral oil was removed by three washes of petroleum ether (300 ml each).

Workup

The hydrated dextran microspheres were suspended in 500 ml of 95% aqueous ethanol, and the mixture was adjusted to a pH of 7.0. The supernatant was decanted off, followed by further dehydration of the microspheres with two 500 ml washes of 95% ethanol, and one final wash with 500 ml absolute ethanol. The product was then filtered and dried to yield (typically) 2.6–3.2 gms of a white, free flowing powder. The size and the general morphology of the microspheres were examined under a scanning electron microscope.

Tables

Tables I-A, I-B and I-C below show dextran molecular weight and quantities of other reactants in the batches prepared in accordance with this example. Each Table gives the data for one series. Headings show parameters that remain constant throughout a series. The amount of dextran (3.6 g) and the quantity of water to dissolve dextran (15.6 ml) are constant throughout all three series shown in Tables I-A, I-B and I-C. Crosslinking density is varied by varying the amounts of cyanogen bromide and NaOH. Crosslinking density is measured by the mole ratio of cyanogen bromide to dextran hydroxyl groups (the CNBr:dextran-OH group mole ratio) as discussed earlier. The mole ratio of CNBr to NaOH is always substantially 1:1. "Total Water" in the tables below denotes the total quantity of water added with the three reactants (dextran, CNBr and NaOH). The last row in each table, "Mole Ratio" denotes CNBr/dextran-OH mole ratio and is the ratio of moles of CNBr to moles of hydroxyl groups in the dextran polymer. Notes which apply to all three tables follow Table I-C.

TABLE I-A

| Series A: Dextran MW 515,000; CNBr dissolved in 8 ml of water | | | | |
| --- | --- | --- | --- | --- |
| Batch No. | 39 | 45 | 46 | 36 |
| CNBr, gms | 0.15 | 0.30 | 0.60 | 1.5 |
| CNBr, mmole | 1.42 | 2.83 | 5.66 | 14.2 |
| 10M NaOH, ml | 0.144 | 0.288 | 0.576 | 1.44 |
| Water (A), ml | 15.6 | 15.6 | 15.6 | 15.6 |
| Water (B), ml | 8 | 8 | 8 | 8 |
| Total water, ml (C) | 23.7 | 23.9 | 24.2 | 25.0 |
| CNBr conc., moles/L | 0.060 | 0.118 | 0.234 | 0.568 |
| NaOH conc., moles/L | 0.061 | 0.121 | 0.238 | 0.5 |
| CNBr/dextran-OH mole ratio | 0.021:1 | 0.042:1 | 0.084:1 | 0.21:1 |

TABLE I-B

| Series B: Dextran MW 515,000; CNBr dissolved in 16 ml of water | | | | |
| --- | --- | --- | --- | --- |
| Batch No. | 38 | 42 | 43 | 44 |
| CNBr, gms | 0.15 | 0.3 | 0.6 | 1.5 |
| CNBr, mmoles | 1.42 | 2.83 | 5.66 | 14.2 |
| 10M NaOH, ml | 0.144 | 0.288 | 0.576 | 1.44 |
| Water (A), ml | 15.6 | 15.6 | 15.6 | 15.6 |
| Water (B), ml | 16 | 16 | 16 | 16 |
| Total water, ml (C) | 31.7 | 31.9 | 32.2 | 33.0 |
| CNBr conc., moles/L | 0.045 | 0.089 | 0.176 | 0.430 |
| NaOH conc., moles/L | 0.045 | 0.090 | 0.179 | 0.436 |
| CNBr/dextran-OH mole ratio | 0.021:1 | 0.042:1 | 0.084:1 | 0.21:1 |

TABLE I-C

| Series C: Dextran MW 40,000; CNBr dissolved in 16 ml of water | | |
| --- | --- | --- |
| Batch No. | 48 | 47 |
| CNBr, gms | 0.6 | 1.5 |
| CNBr, mmoles | 5.66 | 14.2 |
| 10M NaOH, ml | 0.576 | 1.44 |
| Water (A), ml | 15.6 | 15.6 |
| Water (B), ml | 16 | 16 |
| Total water, ml (C) | 32.2 | 33.0 |
| CNBr conc., moles/L | 0.176 | 0.430 |
| NaOH conc., moles/L | 0.179 | 0.436 |
| CNBr/dextran-OH mole ratio | 0.084:1 | 0.21:1 |

Notes:
(A) Water to dissolve dextran
(B) Water to dissolve CNBr
(C) Total water to dissolve reactants (dextran CNBr and NaOH)

Notes on Preparation

At the end of the petroleum ether wash, after all of the petroleum ether has been decanted off, an aqueous phase which contains a water insoluble solid phase (indicative of crosslinked polymer) remained. This insoluble phase was a gel in most batches. In batches 38 and 39, which have low crosslinking densities (0.021), the products included a water insoluble gel which tended to agglomerate and which required high shear agitation to break up the agglomerates. For highly crosslinked systems, i.e., when the CNBr/OH ratio is 0.21, the aqueous phase may not appear in a gel form, but in a slurry. This slurry will not become a clear solution when more water is added to it, if crosslinking to form beads has taken place. (This is the case in batches 36, 44 and 47 illustrated in Table I above.) The slurry solids will dissolve completely if no crosslinking has taken place, as for example in Comparative Example A which follows.

Observations

Products were observed under the microscope to be in the form of microspheres having varying diameters mostly in the range of about 2 to about 50 microns.

The final products in batches 38 and 39 were in the form of irregularly shaped aggregates. The final products in all other runs described in this example were in the form of discrete beads or microspheres.

Analysis

Analysis of a sample of the final product of batch number 46 for nitrogen showed a nitrogen content of 1.09% by weight. This compares with a theoretical nitrogen content of 2.1% by weight. The actual nitrogen content is 52% of theoretical.

Samples of beads from each batch were tested for cyanide, which in all cases was found to be absent at levels higher than 1 ppm (the limit of detection of the test used). A colorimetric assay was performed on an aqueous extract of microspheres (100 mg microspheres in 10 ml distilled water).

Comparative Example A

This comparative example illustrates conditions under which no beads or microparticles are formed.

Three batches are illustrated in this comparative example. The procedure of Example I was followed, except that dextran molecular weight and reactant quantities and ratios were as shown in Table II below. The mole ratio of NaOH to CNBr varied from one batch to another in this example, as shown in Table II below. (The mole ratio of NaOH to CNBr was constant at substantially 1:1 throughout all series in Example I.) It will be noted that the procedure used to prepare batch number 40 is the procedure of Example I, Series C. CNBr was dissolved in 16 ml of water in all batches in this comparative example. The quantity of non-crosslinked dextran starting material was 3.6 g in all batches.

TABLE II

| Batch No. | 40 | 9 | A |
|---|---|---|---|
| Dextran MW (add 000) | 40 | 515 | 515 |
| CNBr, gms | 0.15 | 0.3 | 1.5 |
| CNBr, mmoles | 1.42 | 2.83 | 14.2 |
| 10 M NaOH, ml | 0.144 | 1.5 | 0 |
| Water (A), ml | 15.6 | 15.6 | 15.6 |
| Water (B), ml | 16 | 16 | 16 |
| Total water, ml (C) | 31.7 | 33.1 | 31.6 |
| CNBr conc., moles/L | 0.045 | 0.085 | 0.449 |
| NaOH conc., moles/L | 0.045 | 0.453 | 0 |
| CNBr/dextran-OH mole ratio | 0.021:1 | 0.042:1 | 0.21:1 |
| NaOH/CNBr mole ratio (D) | 1:1 | 5:1 | 0 |

Notes:
(A) Water to dissolve dextran
(B) Water to dissolve CNBr
(C) Total water to dissolve reactants
(D) Nominal; actual varies slightly (except in Batch A)

In batch number 40, the aqueous layer separated from the mineral oil layer even before washing. This aqueous layer was completely water soluble, indicating formation of no insoluble crosslinked beads.

The mole ratio of NaOH to CNBr in batch number 9 was approximately 5:1 instead of the essentially 1:1 used in batch number 40 and in all of the batches described in Example I above. These conditions failed to give microparticles. Also, the aqueous layer after petroleum ether wash and decanting of petroleum ether was solids free, indicating that no crosslinking has taken place.

Microspheres were likewise not obtained when the mole ratio of NaOH to CNBr is essentially 2:1. This will be illustrated in Example VII.

In Comparative Run A, no sodium hydroxide was added. No beads were observed and the aqueous phase was completely free of solids, indicating that no crosslinking had taken place. This shows that addition of alkali as well as CNBr is necessary in order to obtain the desired crosslinked polymer product.

A conclusion from the studies shown in Example I and Comparative Example A is that higher molecular weight dextran can be crosslinked to form microparticles using lower amounts of crosslinking agent. Higher molecular weight dextran in Example II (molecular weight 515,000) gives crosslinked polymer product at all crosslinking ratios tested. On the other hand, lower molecular weight dextran (e.g., MW 40,000) gives a crosslinked product using higher amounts of crosslinking agent as in batches 47 and 48 of Example II while crosslinking does not take place using lower amounts of the crosslinking agent, as illustrated in batch number 40 in Comparative Example A.

Example II

This example describes an alternative workup procedure.

Microspheres of crosslinked dextran were prepared according to the procedure of Example I.

Workup was carried out as follows:

500 ml of distilled water was added to the beads and the suspension was acidified to a pH of 3.0 with HCl. The mixture was stirred gently, and maintained at 35°–40° C. for 30 minutes and is then neutralized to a pH between 6.5–7.0 using aqueous NaOH. The suspension was then centrifuged and the aqueous supernatant was discarded. The beads were then washed in a blender with 500 ml of distilled water, and then centrifuged again. The supernatant was discarded, and the beads were added to 500 ml of 95% ethanol and then stirred in the blender using high shear, which action separates the particles from each other. The suspension was allowed to settle, and the alcohol supernatant rejected. The product was finally vacuum filtered and then dehydrated with 200 ml of absolute ethanol of acetone. Typical product yield is 1.9 gms.

Example III

Microparticles of crosslinked dextran, prepared from dextran of 515,000 MW, were prepared according to the procedure of Example I, except that heating of the mixture following acidification with HCl during workup is omitted; instead, the mixture was acidified with HCl and immediately taken to a neutral pH. No detectable levels of cyanide were found on the final microparticles or beads. This suggests that any cyanide that might be formed is eliminated during workup. It appears that the decomposition of cyanogen bromide to the cyanide ion does not occur to an appreciable extent.

Example IV

The procedure of Example I was followed except that the amount of acid added to the suspension of hydrated microspheres in 95% ethanol was sufficient only to adjust the pH of the suspension to about 7.0, rather than to 2 to 3 as in Example I. A series of crosslinked microspheres having different crosslinking densities were prepared in this manner. The products were obtained as dry, free flowing powders. Product yields are typically from 2.6 to 3.2 grams.

Colorimetric analysis of an aqueous extract of product microspheres (100 mg of microspheres in 10 ml. of water) showed that cyanide is absent at levels higher than 1 ppm (the detectable limit).

It is not necessary to acidify the microspheres/ethanol mixture during workup to an acid pH (say 2–3) since cyanide is not formed to a large extent as shown in Example III. It is sufficient to neutralize the bead/ethanol mixture as illustrated in this example in order to obtain a pharmaceutically acceptable product.

Example V

This example describes experiments carried out to determine the hydrolytic degradability (and hence potential biodegradability) of microspheres or beads prepared according to this invention.

All beads described in this example were prepared from water soluble dextran having an average molecular weight of 515,000. The beads were those prepared according to Example I, Series A and B.

The following uniform test procedure was used.

100 mg of beads (or microspheres) prepared according to Example I and 10 ml of phosphate buffered saline (PBS) of pH 7.4 were charged to graduated glass or plastic tubes, forming an aqueous suspension. The pH of the aqueous suspension was 7.3–7.4. The tube was capped with a fluid tight cap and the tube and its contents were allowed to stand at ambient temperature (25° C.) for 24 hours. The tube was then shaken and the contents allowed to settle. The volume of suspended beads (the opaque portion of the tube contents, which was near the bottom of the tube) was read and recorded. This is reported as "initial bead volume" in the tables which accompany this example.

Bead volumes at this stage vary inversely with crosslinking density, as shown by the tables which accompany this example and the figures of drawing which are referred to in this example. In other words, beads of low crosslinking density swell to a greater extent in PBS at ambient temperature than do beads of higher crosslinking density. Only small differences in swellability are observed when the crosslinking agent (CNBr) is used in different concentrations (in 8 ml vs. 16 ml of aqueous solution) at equal crosslinking densities (moles of CNBr per mole of dextran-OH groups).

Two series of swelling and degradation tests, one at 38° C. (which is close to normal body temperature), the other at 60° C. (an accelerated swelling-degradation test), were carried out as follows: The capped tube was heated to 38° C. or 60° C. and maintained at this temperature for the duration of the test. The time at the start of heating is taken as zero. (Initial bead volume is therefore the bead volume at time= zero.) The bead volume (the opaque white portion of the tube contents) was read and recorded periodically, i.e. every 24 or 48 hours. The beads swelled in water until maximum bead volume is reached. Upon further heating in water, the bead volume diminished, indicating that dissolution was taking place. (Redissolution and swelling presumably take place simultaneously during the first portion of the test, until maximum bead volume is reached.) Complete redissolution of the beads during the course of the test was achieved in some but not all cases.

Time required for complete degradation to non-crosslinked polymer, as well as times to maximum of volume of swollen beads, varies markedly with the degree of crosslinking of the polymer and with treatment temperature. Longer swelling and degradation times are associated with more highly crosslinked polymers. Samples from each batch swell slowly in more highly crosslinked polymers and rapidly in less higher crosslinked polymers, from the initial volume of swollen beads (at time zero) to the peak volume of swollen beads. Most curves also exhibit a plateau region, in which there is little or no change of volume of swollen beads with time, when the peak volume of swollen beads is reached. (This plateau region is not present in the least crosslinked polymers.) The swollen beads then redissolve on further heating. Products of redissolution are the parent (or starting) water soluble dextran, carbon dioxide and ammonium ions, all of which are non-toxic at the concentrations formed on decomposition of the beads.

Results are shown in Tables III-A through III-D below and in FIGS. 1–4. Bead volumes are in milliliters and times are in hours in these tables. Each of the FIGS. 1–4 is a graph showing bead volume in milliliters as a function of time in hours.

TABLE III-A

Swelling and Degradation at 38° C.
Series A
Dextran MW 515,000; CNBr dissolved in 8 ml of water

| Batch No. | 39 | 45 | 46 | 36 |
|---|---|---|---|---|
| CNBr/dextran-OH mole ratio | 0.021 | 0.042 | 0.084 | 0.21 |
| Initial Bead Volume | 2.4 | 1.8 | 0.9 | 0.9 |
| Maximum Bead Volume | 4.7 | 5.5 | 3.8 | 2.8 |
| Time to Max. Bead Volume | 144 | 530–720 | 2680 | 2180 |
| Time for Complete Redissolution (Bead Volume = 0) | 1600 | 1920 | (1) | (1) |

(1) Beads not completely redissolved at time of last reading.

The results given in Table III-A above are shown graphically in FIG. 1. It will be noted in FIG. 1 that the microspheres of run batches 36 and 46 did not completely dissolve during the test. Microspheres of batch 36 (the most highly crosslinked in this series) appeared to reach maximum volume at about the time of the last reading (about 3,400 hours). Microspheres of batch 46 reached peak volume at about 2,500–3,000 hours and were diminishing in volume at the time of the last reading.

TABLE III-B

Swelling and Degradation at 60° C.
Series A
Dextran MW 515,000; CNBr dissolved in 8 ml of water

| Batch No. | 39 | 45 | 46 | 36 |
|---|---|---|---|---|
| CNBr/dextran-OH mole ratio | 0.021 | 0.042 | 0.084 | 0.21 |
| Initial Bead Volume | 1.9 | 1.4 | 1.2 | 0.6 |
| Maximum Bead Volume | 5.0 | 5.5 | 3.5 | 4.1 |
| Time to Max. Bead Volume | 48–72 | 48 | 168–240 | 384 |
| Time for Complete Redissolution (Bead Volume = 0) | 120 | 168 | 336 | 528 |

Figure 2:
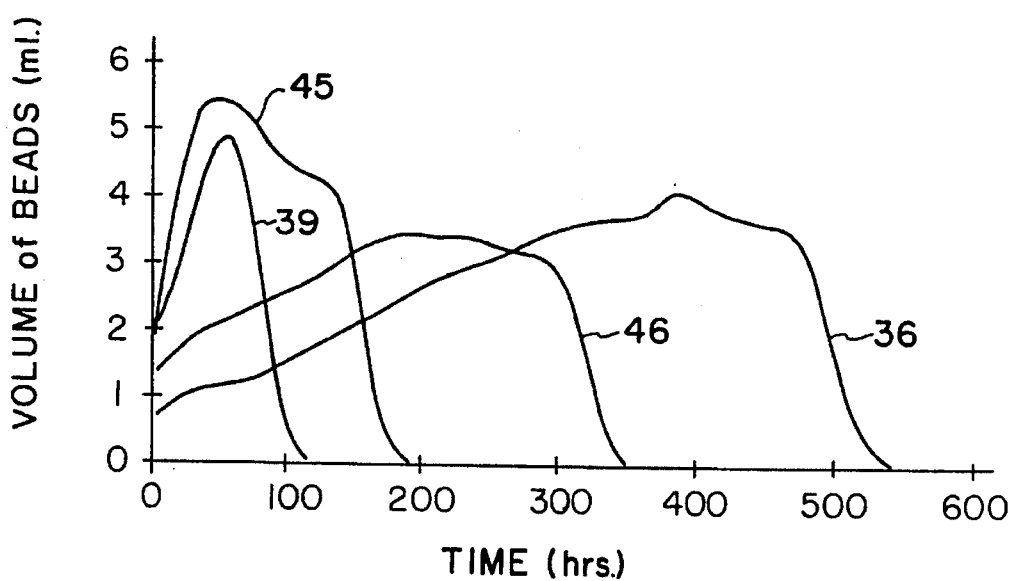
FIG. 2 is a graphical representation of the data in Table III-B.

The results given in Table III-B above are shown graphically in FIG. 2.

TABLE III-C

Swelling and Degradation at 38° C.
Series B
Dextran MW 515,000; CNBr dissolved in 16 ml of water

| Batch No. | 38 | 42 | 43 | 44 |
|---|---|---|---|---|
| CNBr/dextran-OH mole ratio | 0.021 | 0.042 | 0.084 | 0.2 |
| Initial Bead Volume | 2.6 | 1.3 | 0.8 | 0.6 |
| Maximum Bead Volume | 4.6 | 3.2 | 3.6 | 2.4 |
| Time to Max. Bead Volume | 144 | 1,000–1,470 | 3,900 | 3,800 |
| Time for Complete Redissolution (Bead Volume = 0) | 1,700 | 3,900 | (1) | (1) |

(1) Undissolved beads remained at time of last reading.

Figure 3:
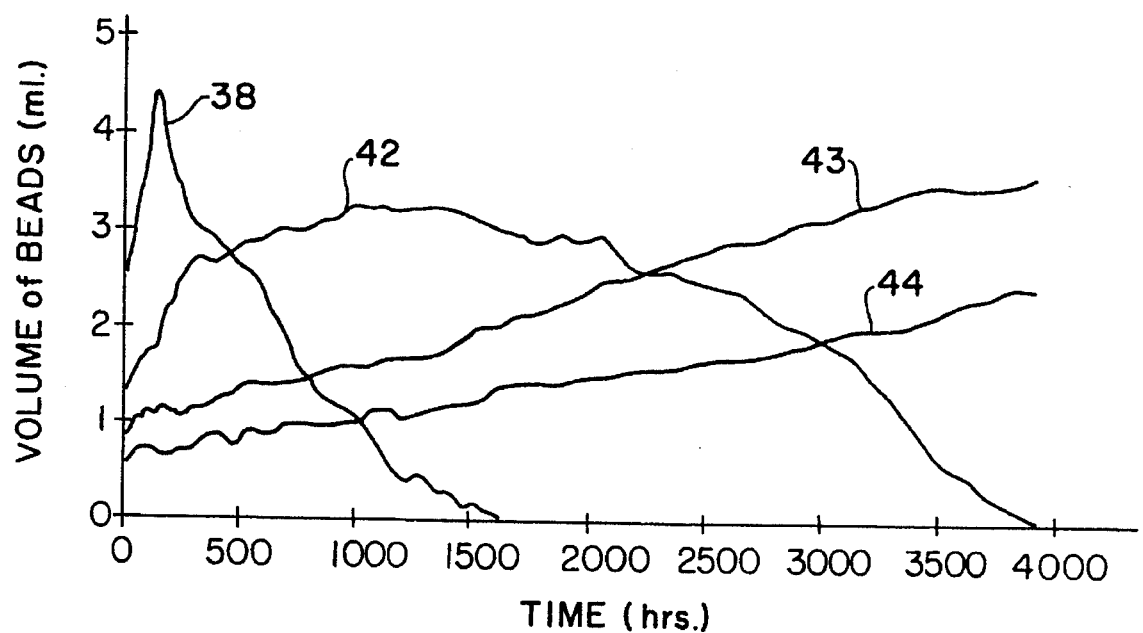
FIG. 3 is a graphical representation of the data in Table III-C.

Results shown in Table III-C above are shown graphically in FIG. 3. It will be noted that the microspheres of batches 42, 43 and 44 did not completely redissolve; in fact, bead volumes in batches 43 and 44 appeared to be reaching a maximum at about the time of or just shortly before the last reading (3,900 hours).

TABLE III-D

Swelling and Degradation at 60° C.
Series B
Dextran MW 515,000; CNBr dissolved in 16 ml of water

| Batch No. | 38 | 42 | 43 | 44 |
|---|---|---|---|---|
| CNBr/dextran-OH mole ratio | 0.021 | 0.042 | 0.084 | 0.21 |
| Initial Bead Volume | 2.2 | 1.0 | 1.0 | 0.6 |
| Maximum Bead Volume | 3.8 | 3.4 | 3.7 | 4.0 |
| Time to Max. Bead Volume | 24 | 72 | 300–420 | 850–900 |
| Time for Complete Dissolution (Bead Volume = 0) | 120 | 240 | 1120 | (4) |

(4) Bead volume 0.8 ml at last reading (1,440 hrs.).

Figure 4:
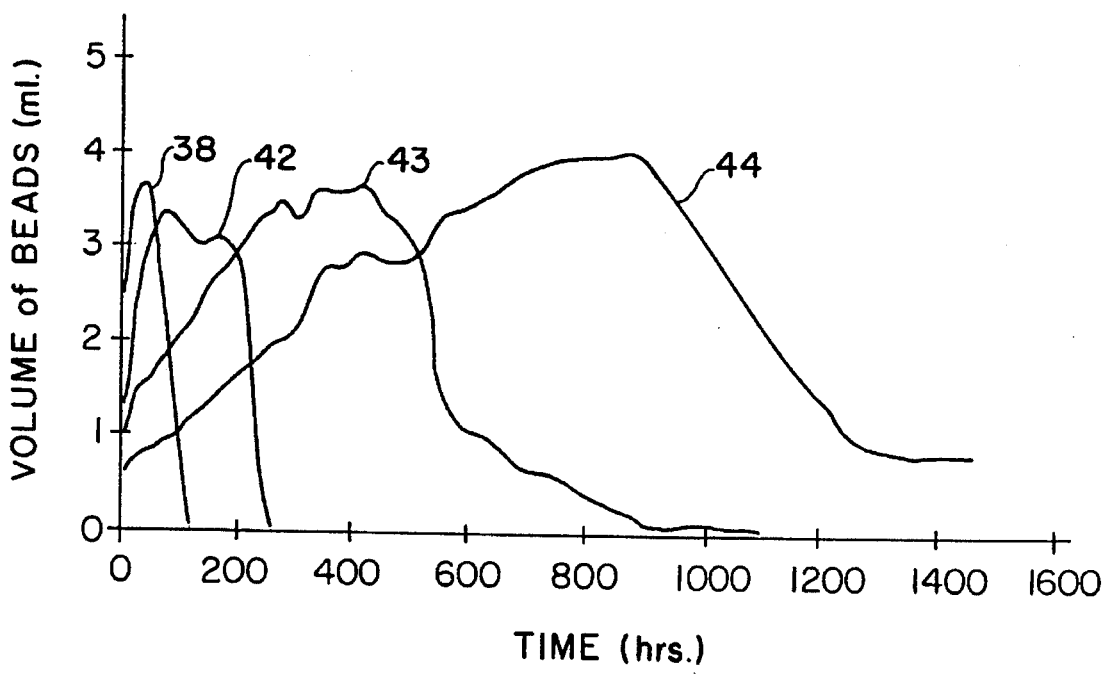
FIG. 4 is a graphical representation of the data in Table III-D.

Results given in Table III-D above are shown graphically in FIG. 4. The microspheres of batches 38, 42 and 43 completely dissolved. However, the microspheres of batch 44 (the most highly crosslinked batch in this series) did not completely redissolve during the duration of this test, and in fact bead volume in this test appeared to have levelled off when the last reading was taken. This is the only instance in which complete redissolution of microspheres at 60° was not achieved.

Comparison of data at 60° with data at 38° C. shows that swelling and degradation take place much faster at 60° C. than at 38° C. Comparison of FIG. 1 and Table III-A with FIG. 2 and Table III-B is invited in this regard. These show behavior of the same compositions at 38° C., and 60° C., respectively. Similarly, FIG. 3 and Table III-C may be compared with FIG. 4 and Table III-D.

Example VI

Beads prepared from water soluble dextran having an average molecular weight of 40,000, according to Example I, Series C, were subjected to the swelling/degradation test of Example V. Results are reported in Table IV below.

TABLE IV

| Batch No. | 48 | 47 | 48 | 47 |
|---|---|---|---|---|
| Temperature, °C. | 38° | 38° | 60° | 60° |
| CNBr/dextran-OH mole ratio | 0.084 | 0.21 | 0.084 | 0.21 |
| Initial Bead Volume | 1.2 | 0.5 | 1.4 | 0.6 |
| Maximum Bead Volume | 2.5 | 2.2 | 2.6 | 2.6 |
| Time to Max. Bead Volume | 280–450 | 2,500 | <18 | 192–216 |
| Time for Complete Redissolution (Bead Volume = 0) | 1,700 | 3,800 | 192 | 400 |

Figure 5:
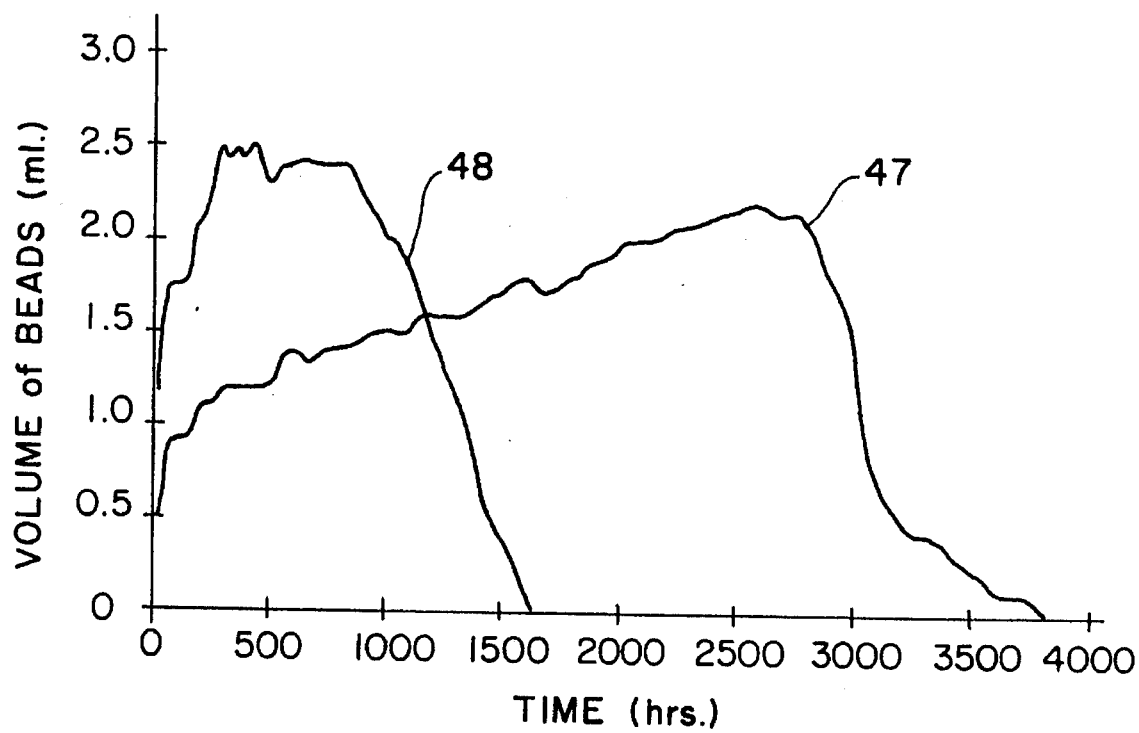
FIGS. 5 and 6 are graphical representations of data in Table IV.
Figure 6:
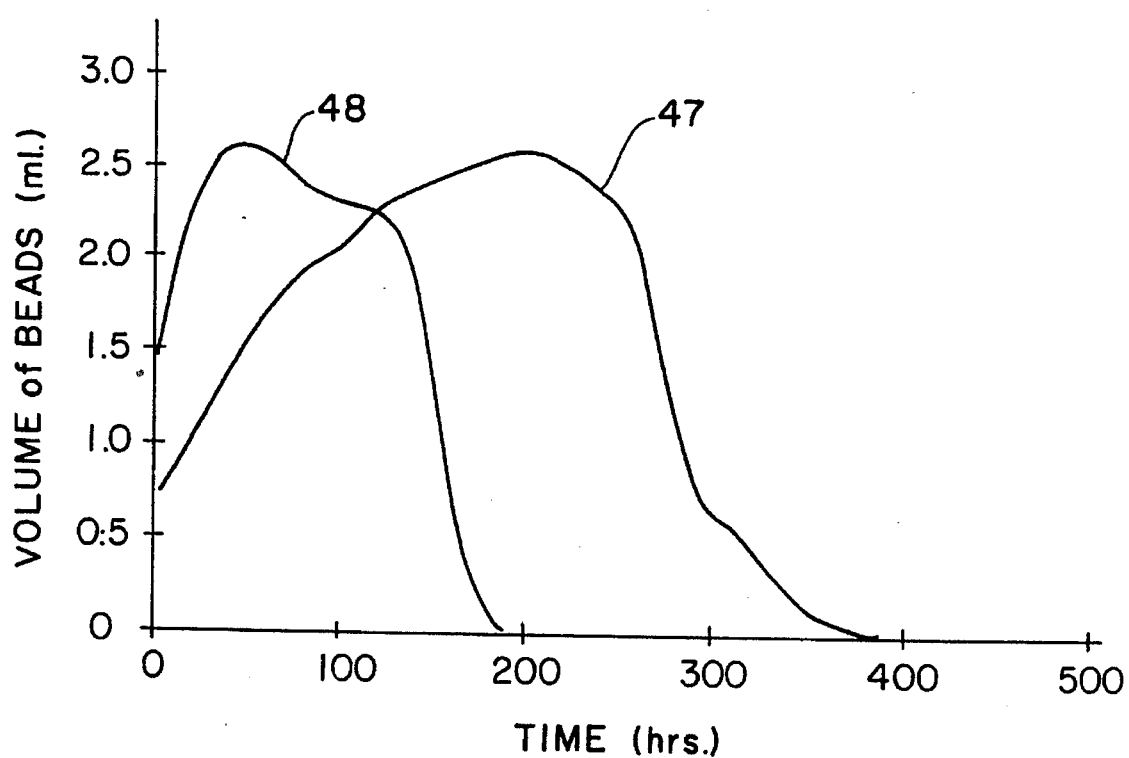

Results shown in Table IV are shown graphically in FIG. 5 (test at 38° C.) and in FIG. 6 (test at 60° C.). Comparison of data at 60° C. with data at 38° C. in Table IV above (and in FIG. 6 and FIG. 5, respectively) shows that swelling and subsequent redissolution take place much faster at 60° C. than at 38° C. Comparison of data in Table IV above and in FIGS. 5 and 6 with data in Table III-A to III-D and in FIGS. 1–4 shows that swelling and subsequent redissolution of crosslinked microspheres prepared from dextran having an average molecular weight of 40,000 proceed much faster than swelling and subsequent redissolution of crosslinked microspheres of the same crosslinking density prepared from dextran having an average molecular weight of 515,000.

Example VII

The procedure of Example I was followed except that operations were carried out on a larger scale.

Two batches were prepared according to this example. The two batches differed only in the mole ratio of NaOH to CNBr.

In batch no. 55, the NaOH/CNBr mole ratio was essentially 2:1. After the petroleum ether wash, the product was a gelatinous mass which could not be dehydrated to microspheres by treatment with 95% ethanol. The experiment was abandoned at this point.

In batch no. 56, the NaOH/CNBr mole ratio was essentially 1:1. Microspheres were attained after workup.

Both runs used water soluble non-crosslinked dextran having an average molecular weight of 515,000 as the starting material.

Table V below shows reactant quantities which were different in the two batches. Quantities which were the same in both batches are shown in the heading for the table.

This example shows that microspheres are not obtained when the mole ratio of NaOH to CNBr deviates substantially from 1:1.

TABLE V

Dextran weight: 10.8 g (200 millimoles)
Dextran M.W.: 515,000
Water to dissolve dextran: 48.6 ml
CNBr: 1.8 g (17.0 millimoles)
CNBr/dextran-OH mole ratio: 0.085
Volume of light mineral oil (petroleum ether): 400 ml

| Batch No. | 55 | 56 |
|---|---|---|
| CNBr/dextran-OH mole ratio | 0.085 | 0.085 |
| CNBr, g | 1.8 | 1.8 |
| CNBr, mmoles | 17.0 | 17.0 |
| NaOH, 10M, ml | 3.6 | 1.8 |
| Microspheres? | No | Yes |

Example VIII

Part A—Preparation and Workup of Microspheres

This example describes a still larger scale preparation of crosslinked dextran microspheres having compositions similar to those described in Example I.

Starting materials for this example were water, dextran having an average molecular weight of 40,000 and water soluble dextran having an average molecular weight of 515,000.

The quantity of water soluble dextran starting material for all batches described in this example was 36 g (compared to 3.6 g in Example I).

The procedure of Example I was followed, except that (1) quantities of dextran, NaOH and CNBr were scaled up 10:1 compared to Example I and (2) quantities of water (for dissolving dextran and CNBr) and light mineral oil were scaled up, but not proportionately. Quantities of materials used in the example are shown in Tables VI-A and VI-B below. Quantities which were the same in all batches reported in a table are shown at the top of the table.

TABLE VI-A

Dextran Weight: 36 g
Dextran M.W.: 515,000
Volume of Mineral Oil: 600 ml

| Batch No. | 66 | 65 |
|---|---|---|
| CNBr/dextran-OH mole ratio | 0.011 | 0.021 |
| CNBr, g | 0.75 | 1.5 |
| CNBr, mmoles | 7.12 | 14.2 |
| NaOH, 10M, ml | 0.75 | 1.5 |
| Water (A), ml | 60 | 60 |
| Water (B), ml | 20 | 20 |
| Total water, ml | 81 | 81 |
| CNBr conc., moles/L | 0.088 | 0.17 |
| NaOH conc., moles/L | 0.092 | 0.185 |

(A) Water to dissolve dextran
(B) Water to dissolve CNBr

TABLE VI-B

Dextran Weight: 36 g
Dextran M.W.: 40,000
Volume of Mineral Oil: 600 ml

| Batch No. | 63 | 61 | 59 |
|---|---|---|---|
| CNBr/dextran-OH mole ratio | 0.021 | 0.056 | 0.084 |
| CNBr, g | 1.5 | 4.0 | 6.0 |
| CNBr, mmoles | 14.2 | 37.8 | 56.6 |
| NaOH, 10M, ml | 1.5 | 4.0 | 6.0 |
| Water (A), ml | 40 | 78 | 156 |
| Water (B), ml | 20 | 45 | 80 |
| Total Water, ml | 61 | 127 | 242 |
| CNBr, conc., moles/L | 0.233 | 0.298 | 0.234 |
| NaOH, conc., moles/L | 0.245 | 0.315 | 0.248 |

Notes:
(A) Water to dissolve dextran
(B) Water to dissolve CNBr

Workup was as follows: mineral oil was removed by one washing with 500 ml of petroleum ether followed by two successive washings with 300 ml each of petroleum ether. In each washing the mixture was briefly agitated and then allowed to settle. The organic phase was then decanted. Then 1,000 ml of 95% ethanol was added to the aqueous phase and the mixture stirred at high shear. The mixture was acidified to pH 2.0 with HCl and allowed to stand for five minutes without heating. The pH of the mixture was then adjusted to 7.0 with NaOH solution. The supernatant was decanted. The beads were washed once more with 1,000 ml of 95% ether, the supernatant decanted, and the beads washed with 500 ml of absolute ethanol or methanol, then filtered, suction dried and air dried.

The product in all runs was in the form of discrete microspheres. In contrast, the products of batches 38 and 39 (both of which have a crosslinking density or CNBr/dextran-OH mole ratio of 0.021:1) in Example I were in the form of irregularly shaped aggregates. This example shows that products of the present invention can be obtained in the form of discrete microspheres over a wide range of crosslinking densities and with either a high molecular weight (M.W. 515,000) soluble dextran or much lower molecular weight (M.W. 40,000) dextran as the starting material.

Part B—Swelling and Degradation

Swelling and degradation of microspheres prepared according to Part A of this example were determined according to the procedure described in Example V, except that degradation tests are carried out only at 38° C. As in Example V, beads were allowed to swell in PBS at ambient temperature for 24 hours and the swollen volume ("Initial Bead Volume") was then measured. These suspensions were then heated at 38° C. as described in Example V and bead volumes were measured periodically. As in Example V, time at the start of heating (which is immediately after Initial Bead Volume is measured) is taken as zero.

Results are shown in Table VII below. In Table VII, bead volumes are in milliliters and times are in hours.

Figure 7:
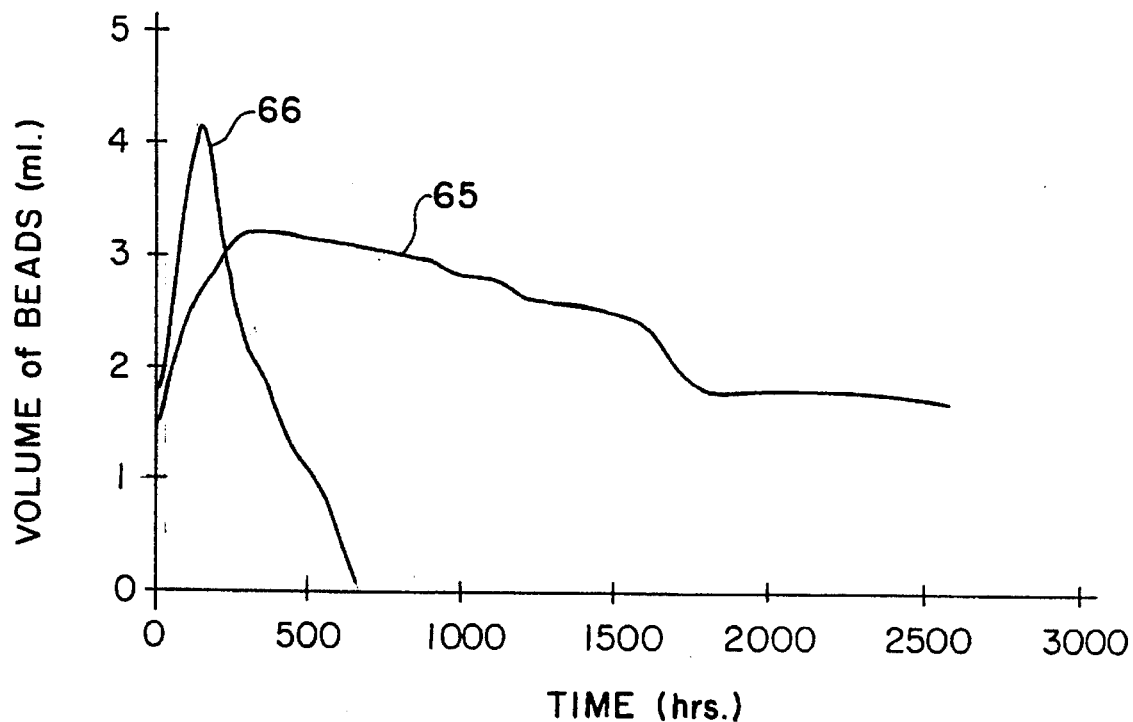
FIGS. 7 and 8 are graphical representations of data in Table VII.
Figure 8:
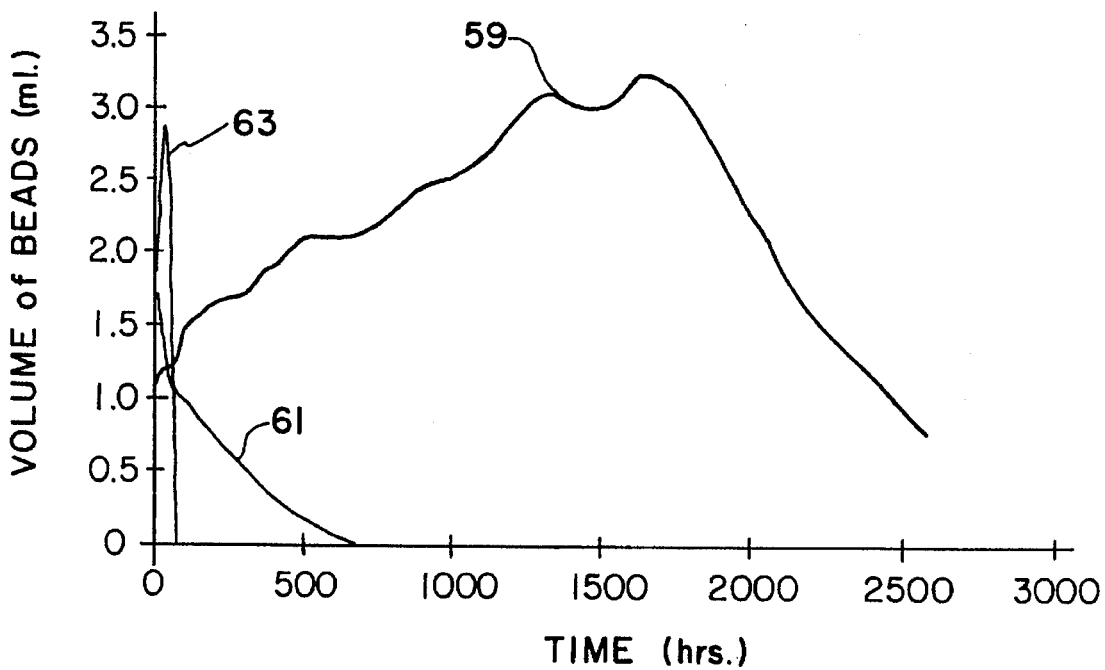

Results are also shown graphically in FIGS. 7 and 8. FIG. 7 shows in graphical form the data for beads prepared from dextran having a molecular of 515,000. FIG. 8 shows in graphical form the data for beads prepared from dextran having a molecular weight of 40,000.

TABLE VII

| Batch No. | 66 | 65 | 63 | 61 | 59 |
|---|---|---|---|---|---|
| Starting Dextran MW | 515,000 | 515,000 | 40,000 | 40,000 | 40,000 |
| CNBr/dextran-OH mole ratio | 0.011 | 0.021 | 0.021 | 0.056 | 0.084 |
| Initial Bead Volume, ml | 1.7 | 1.4 | 1.8 | 1.7 | 1.1 |
| Maximum Bead Volume, ml | 4.2 | 3.2 | 2.9 | 1.7 | 2.5 |
| Time to Max. Bead Volume, hr | 144 | 264–480 | 24–48 | 0 | 1,000 |
| Time for Complete Redissolution, hr (Bead Volume = 0) | 800 | (1) | 96 | 670 | (1) |

(1) Beads did not completely redissolve during test.

Comparison of swelling and degradation data in this example with data for similar compositions in Examples V and VI (specifically batch 65 in this example vs. batches 39 and 38 in the other examples, and batch 59 in this example vs. batch 48 earlier) show that compositions having the same starting dextran molecular weight and the same CNBr:dextran-OH mole ratio (which is indicative of crosslinking density) made according to Example VIII have longer degradation times than do similar compositions made according to Example I. This suggests that cyanogen bromide is used more efficiently in forming crosslinking groups in the activation procedure of Example VIII than in the activation procedure of Example I.

Example IX

The procedure of Example VIII is followed except that the mixture of beads as formed, aqueous phase and 95% ethanol is neutralized, to pH 7.0 during workup instead of being acidified to pH 2 and then neutralized. The product is recovered as a dry, free flowing powder in the form of microspheres.

Example X

This example describes an acute toxicity test.

Buffered solutions containing degraded dextran polymer (from Example V) were injected into adult Sprague-Dawley rats weighing 600–700 grams. No mortality was seen and no visible changes were observed after 180 days. Results demonstrate that the degradation (or hydrolysis) products of the microspheres of this invention are non-toxic.

Example XI

This example describes tests of an experimental wound dressing according to this invention and a comparative wound dressing (which is a commercial product) on test animals.

Dressings studied:

1. An experimental hydrocolloid dressing, code named DBD, prepared according to this invention (batch number 66, Example VIII) and containing 17% by weight of microparticles of crosslinked dextran and 83% by weight of an adhesive and pharmaceutically acceptable amorphous polymeric matrix.

2. "Duoderm" CGF, a commercial hydrocolloid dressing made and sold by Convatec, division of Bristol-Myers Squibb, Lawrenceville, N.J., U.S.A.

A second commercial hydrocolloid dressing was included in the study but gave consistently poorer results than either the experimental hydrocolloid dressing or "Duoderm" CGF.

Specific aim of this study:

The aims of this study is to compare the dressings listed above in a wound environment. Macroscopic parameters such as rate of wound closure and the degree of dressing disintegration were studied. Histological examination was done to examine the degree of inflammation and foreign body reaction.

Protocol:

Three female domestic pigs, weight and age matched, were used for this study. Eight full thickness wounds, each 2.5 cm in diameter, were made per animal, symmetrically distributed about the spine (four on each side of the spine) were made using a template, on the flanks of 5 cms away from the midline. Bleeding was controlled with sterile surgical gauze. Following the cessation of bleeding, experimental and control dressings (two inches square), were applied to the wounds in a randomized fashion. Dressings were secured by four sutures through the skin, one in each corner. Each flank was then covered with a strip of adhesive foam to protect the dressings and further cushion the wound sites.

Dressings were changed on days 3, 6, 10, and 14. The detached dressings were checked for disintegration by visual inspection. Wounds were examined for presence of dressing components in the wound beds, and then rinsed with sterile saline to remove any loose dressing residues. The wound beds were not otherwise disturbed. The areas surrounding the wound beds were cleaned with sterile saline-soaked gauze. Fresh dressings were applied and secured to the wound, as on day zero.

On day zero and at the time of the dressing changes (days 3, 6, 10, 14 and 18), a ruler was placed along the side of each wound. A color camera video (JVC), in conjunction with a Gateway 386 PC, a Color Frame Grabber (Data Translation 2871) and a Video Encoder (Data Translation 2879) were used to acquire the wound images. Two blinded reviewers processed each image with Global Lab Color Image Analysis software (Data Translations, Marlboro, Mass.) to calculate area and perimeter data. All images were stored on video tape (Hitachi 5751 VCR). For each image, the Gilman parameter was calculated as will be described below.

On day 18, the pigs were anesthetized with halothane and subsequently euthanized by an intravenous injection of saturated potassium chloride solution. The wound tissues were excised, including two centimeters of uninjured skin surrounding each wound. Wounds were bisected for the convenience of histologic processing and both halves submitted for tissue processing. Specimens were fixed in neutral formalin, embedded in paraffin wax, sectioned at five micrometers, and then stained with hematoxylin and eosin and Masson's trichrome stain.

Slides were numerically coded, and then examined by a pathologist who was blinded to the treatment groups. Each section was scored for ten histologic parameters as shown in Table VIII below. The grading system was devised to objectively and separately rate parameters deemed by the authors to be important in wound healing including re-epithelialization, epithelial thickness, and dermal collagenization. Eschar formation and neovascularity were added to indicate retarded healing. The extent and type of inflammation were evaluated by roughly quantifying acute inflammation, chronic inflammation, foreign material, and presence of foreign body giant cells. Lotus 1-2-3 (Version 2.3) was utilized for data base management. All statistical evaluations were performed by Analysis of Variance (ANOVA).

TABLE VIII

| Parameter | Definition/Description | Scale of Measurement |
| --- | --- | --- |
| 1. Incision width | Measured from center of wound to lateral extent of reactive epithelium, then doubled. | mm |
| 2. Reepithelialization | Estimates % of incision width re-epithelialized | 0 = <25%<br>1 = 25–50%<br>2 = 50–75%<br>3 = 75–99%<br>4 = 100% |
| 3. Thickness of epithelium | Measured from top of dermal papillae to surface including parakeratotic areas. Eukeratotic areas excluded. | mm |
| 4. Eschar formation | Sloughing | 0 = absent<br>1 = present<br>2 = marked |
| 5. Collagen organization | Tissue stained predominantly red (fibroblasts)<br>Tissue stained more red than blue<br>Tissue stained more blue than red<br>Tissue stained predominantly blue (collagen) | 0 = <25% collagen<br>1 = 25–50% collagen<br>2 = 50–75% collagen<br>3 = >75% collagen |
| 6. Acute inflammation | Estimates relative presence of neutrophils | 0 = absent<br>1 = mild<br>2 = moderate<br>3 = marked |
| 7. Chronic inflammation | Estimates relative presence of lymphocytes, eosinophils | 0 = absent<br>1 = mild<br>2 = moderate |

TABLE VIII-continued

| Parameter | Definition/Description | Scale of Measurement |
|---|---|---|
| | | 3 = marked |
| 8. Neovascularity | Histologically similar to adjacent non-reactive dermis | 0 |
| | Increased vascularity | 1 |
| | Markedly increased vascularity | 2 |
| 9. Foreign material | Non-fatty foreign material present on hematoxylin and eosin stained-sections | 0 = absent |
| | | 1 = mild |
| | | 2 = moderate |
| | | 3 = marked |
| 10. Foreign body giant cells | Estimates relative presence | 0 = absent |
| | | 1 = mild |
| | | 2 = moderate |
| | | 3 = marked |

Results:
1. Evaluation of Dressings:

Major differences were seen among the dressing surfaces in contact with the wound exudates. No grossly visible disintegration could be detected in the DBD dressings throughout the period of wound healing. The early, exudative phase of healing (day 0–day 6) caused limited, but visible, disintegration of the DuoDERM CGF, wound contact surfaces. In the later phases of healing (day 10 on) very little disintegration was apparent.

2. Macroscopic Wound Evaluations:

Wounds treated with DBD displayed pink, healthy surfaces. The wounds were largely free of extraneous matter throughout the healing, except on day 6, when a thin, superficially white layer was found to cover the wound surface. This layer, without exception, easily detached with the dressing from the wound on day 10.

Upon visual inspection, wounds treated with DBD, or DuoDERM CGF were essentially free of dressing residues in the later phases of healing (day 10 on). In the early, exudative phases of healing, small but variable quantities of dressing residues were found on wounds treated with these dressings. In the course of the study, none of the wounds in any treatment group appeared to be infected.

3. Rate of Wound Closure and Gilman Parameter

The rates of wound closure, calculated as percentage of wound area healed and as the Gilman parameters from the image analyses, are shown in Table IX below. Values shown are mean values and standard deviations.

TABLE IX

| | DBD | | DuoDERM CGF | |
|---|---|---|---|---|
| Day | % closed | Gilman parameter | % closed | Gilman parameter |
| Day 3 | 3 ± 11 | 0.02 ± 0.05 | 4 ± 16 | 0.03 ± 0.08 |
| Day 6 | 15 ± 24 | 0.09 ± 0.13 | −1 ± 36 | 0.02 ± 0.16 |
| Day 10 | 72 ± 13 | 0.47 ± 0.13 | 65 ± 19 | 0.40 ± 0.16 |
| Day 14 | 92 ± 6 | 0.74 ± 0.16 | 89 ± 10 | 0.64 ± 0.14 |
| Day 18 | 97 ± 5 | 0.88 ± 0.11 | 94 ± 6 | 0.76 ± 0.14 |

For each image, the Gilman parameter was calculated by the following equation:

$$\bar{d} = \Delta A / \bar{p}$$

where $\Delta A$ is the change in the area of wound healed compared to the original wound cross-sectional area after study time T, $\bar{p}$ is the average of the wound perimeter (in mm) before and after time T, and $\bar{d}$ represents the distance (in mm) of advance of the wound margin toward the wound center over the study time T. The Gilman parameter is useful in normalizing natural differences in wound sizes and shapes. Statistical comparisons of the mean Gilman parameters among wounds treated with the different wound dressings were performed by Analysis of Variance (ANOVA). A SAS General Linear Models Procedure was run to test for variance between groups at the p=0.05 level.

The Gilman parameter is described in "Wounds", vol. 2, no. 3, pgs. 95–101, 1991.

Complete wound closure by day 18 occurred for more DBD than DuoDERM CGF dressings, although the difference was significant only at one evaluation point (Gilman parameter, day 18).

4. Histologic Evaluation:

The microscopic examination of the healed tissues yielded the most information about the relative efficacies of the dressings in promoting wound healing. The numerical data used to support the descriptive statements in the following sections are summarized in Table X. Values shown in Table X are mean values. The "code" was broken after all slides had been evaluated by a pathologist. Rankings (applicable to all parameters in Table X except incision width and thickness of epithelium) are explained earlier in connection with Table VIII.

TABLE X

| Parameter | Duoderm CGF | DBD |
|---|---|---|
| Incision width, mm | 10.47 | 9.69 |
| Re-epithelialization | 3.38 | 3.56 |
| Thickness of epithelium, mm | 0.03 | 0.046 |
| Eschar formation | 0.13 | 0.13 |
| Collagen organization | 2.38 | 2.69 |
| Acute inflammation | 0.31 | 0.31 |
| Chronic inflammation | 1.31 | 1.00 |
| Neovascularity | 0.94 | 0.81 |
| Foreign material | 0.25 | 0.31 |
| Foreign body giant cells | 1.06 | 0.63 |

The percentage of sections having foreign body giant cells was as follows: Duoderm CGF, 74%; DBD, 38%.

DBD Treatment Group: The majority of the sections demonstrated complete re-epithelialization with a mature appearing keratinized squamous epithelium, some with eschar formation. Collagenization was very organized, interrupted only by small collections of foreign giant body cells. Where inflammation was present, it was scant but consisted of both acute and chronic inflammatory cells. Neovascularization was minimal and superficial; giant cells were scattered and few. Foreign material, as well, was rarely identified.

Duoderm CGF Treatment Group: In the majority of the sections, re-epithelialization was less complete than DBD and consisted of a squamous epithelium which was thin and immature. Eschar formation was focal. Collagenization was organized but more cellular than DBD treated wounds. Acute and chronic inflammatory cells were present in moderate amounts in a patchy distribution while neovascularization was moderate in amount. Foreign body giant cells were prominent; identifiable foreign material was not.

The data assembled in Table X were evaluated statistically between dressings for each histological parameter. Epithelial thickness was 0.03 mm in Duoderm and 0.046 mm in DBD. Conclusions of This Study:

DBD performs statistically better than Duoderm CGF in the key parameters evaluated, i.e., epithelial thickness, degree of epithelialization, reduction of foreign body type reaction, and attenuation of chronic inflammation. The key advantage to a system like DBD, over an established market leader like Duoderm CGF is the reduction in chronic inflammation due to the potential biodegradability of the absorptive component used in the dressing.

Example XII

Preparation of arginine grafted beads:

To a solution of 6 gms of dextran (515,000 MW) in 500 ml of water the following were added sequentially: 4 ml 10M NaOH, 4 gms CNBr/100 ml water, and 13.6 gms arginine/100 ml of water. The pH was adjusted to 9.0, and the reaction continued for 16 hours. The pH was then adjusted to 7.0, and the solution dialyzed against cold water for 48 hours to eliminate unreacted arginine and other soluble low molecular weight components. The solution was then concentrated to 30 ml; the arginine grafted dextran was then crosslinked as described above, in 300 ml of light mineral oil, using 7 ml of 10M NaOH and 7 gms of cyanogen bromide in 70 ml of water. Following removal of mineral oil with petroleum ether, the microspheres were suspended in 500 ml of water, the pH adjusted to 7.0, and then centrifuged. The residue was washed with 3×400 ml water, followed by dialysis against running water for 48 hours to eliminate all soluble and leachable components. The product was finally dehydrated with anhydrous alcohol to yield 6.7 gms of free flowing microspheres.

The arginine grafted microspheres contained 26.3% w/w arginine.

Example XIII

Synthesis of Dextran Sulfate:

Dextran sulfates of various sulfur concentrations were prepared according to published procedures, except that sulfur trioxide:dimethyl formamide (DMF) complex was used instead of the sulfur trioxide:formamide complex reported in the literature. The starting material was dextran having an average molecular weight of 40,000. Amounts of $SO_3$-DMF complex per gram of dextran ranged from 1.0 to 4.0, and the degrees of sulfation of the resulting products range from 0.5906 to 2.894. Degree of sulfation was approximately but not precisely linear based on quantity of $SO_3$-DMF complex reactant.

Table XI below shows quantities of $SO_3$-DMF complex reacted and resulting degrees of sulfation in batches prepared in accordance with this example. Quantities of $SO_3$-DMF complex are given in grams of $SO_3$-DMF complex per gram of dextran (i.e., gm/gm) in Table XI.

TABLE XI

| | Dextran M.W.: 40,000 | |
|---|---|---|
| Batch No. | $SO_3$-DMF gm/gm | Degree of Sulfation |
| DS11 | 1.0 | 0.5906 |
| DS10 | 1.55 | 0.6116 |
| DS9 | 2.0 | 1.311 |
| DS12 | 4.0 | 2.894 |

Crosslinking of Dextran Sulfate:

Dextran sulfate microspheres of various sulfur contents, prepared as described in the preceding paragraph, were crosslinked by reaction with NaOH in CNBr according to methods described earlier herein.

Table XII below shows representative batches (or runs) in which sulfated dextrans, prepared as described above in this example, were crosslinked by reaction with quantities of NaOH and CNBr. Quantities of 10M NaOH and CNBr are shown in Table XII in milliliters per gram of dextran (ml/gm) and grams per gram of dextran (gm/gm), respectively. Table XII also shows whether or not microspheres were obtained.

TABLE XII

| Batch No. | $SO_3$-DMF gm/gm | 10M NaOH ml/gm | CNBr gm/gm | Microspheres? |
|---|---|---|---|---|
| DS9C1 | 2.0 | 0.4 | 0.25 | Yes |
| DS9C2 | 2.0 | 0.4 | 0.4 | Yes |
| DS9C3 | 2.0 | 0.75 | 0.75 | Yes |
| DS10C2 | 1.55 | 0.4 | 0.25 | Yes |
| DS11C1 | 1.0 | 0.4 | 0.15 | Yes |
| DS10C3 | 1.55 | 0.15 | 0.15 | No |
| DS11C2 | 1.0 | 0.4 | 0.08 | No |
| DS12C1 | 4.0 | 0.4 | 0.25 | No |

As data in Table XII show, the mole ratio of NaOH to CNBr could be varied considerably from the ratio (essentially unity) applied to crosslink unsubstituted dextran. (Runs DS9C1, DS9C3 and DS11C1, in which the NaOH/CNBr mole ratios were about 1.6, 1.6 and 2.8, respectively, show this.) Also, a much higher preparation of base to dextran could be tolerated.

Swelling and degradation rates of dextran sulfate microspheres bear the same inverse relationship to the CNBr:dextran-OH mole ratio as was observed in microspheres prepared from unsubstituted dextran.

The present invention provides, in microsphere form, a crosslinked dextran polymer which is water insoluble at ambient temperature (25° C.) but degrades into water soluble products (including non-crosslinked dextran) on prolonged exposure to aqueous fluids (including body fluids such as blood and lymph) at normal body temperature (37° C.) and higher. Furthermore, these crosslinked polysaccharide microspheres, either alone or when compounded with a suitable hydrophobic matrix material, are capable of absorbing appreciable quantities of aqueous fluids (including aqueous body fluids) at ambient temperature. The combination of absorptivity and hydrolytic degradability (and therefore potential biodegradability) at body temperature make the polysaccharide compositions of the present invention a very desirable component in wound dressings.

While the present invention has been described in detail with particular reference to preferred embodiments thereof, it shall be understood that such description is by way of illustration and not limitation.

What is claimed is:

1. A water swellable and hydrolytically labile crosslinked polymer composition in the form of microspheres, said polymer composition comprising polysaccharide chains and crosslinking groups selected from the group consisting of linear imidocarbonate groups, linear carbonate groups and mixtures thereof, said polysaccharide chains being derived from a water soluble polysaccharide, said polymer composition being essentially free of crosslinking groups other than said imidocarbonate and said carbonate, said polymer composition being water swellable and water insoluble at 25° C. and degradable to a water soluble non-crosslinked polysaccharide in an essentially neutral aqueous medium at a temperature of at least 37° C.

2. A composition according to claim 1, wherein said microspheres have particle diameters predominantly in the range of about 1 micron to about 100 microns.

3. A composition according to claim 2 wherein said microspheres have particle diameters predominantly in the range of about 2 to about 50 microns.

4. A composition according to claim 1 wherein said polysaccharide is dextran.

5. A composition according to claim 1 wherein said crosslinking groups are formed as imidocarbonate groups by treatment of said water soluble polysaccharide with a cyanogen halide in an aqueous alkaline medium.

6. A composition according to claim 5 wherein said cyanogen halide is cyanogen bromide.

7. A composition according to claim 5 wherein said aqueous medium is an aqueous phase of a water-in-oil dispersion.

8. A composition according to claims 5 wherein the quantity of said cyanogen halide is from about 0.01 mole to about 0.25 mole per mole of polysaccharide hydroxyl groups.

9. A composition according to claim 8 wherein the quantity of said cyanogen halide is from about 0.02 mole to about 0.1 mole per mole of polysaccharide hydroxyl groups.

10. A process for preparing a water swellable and hydrolytically labile crosslinked polymer composition in the form of microspheres, wherein said polymer composition comprises polysaccharide chains and crosslinking groups selected from the group consisting of linear imidocarbonate groups, linear carbonate groups and mixtures thereof and is essentially free of other crosslinking groups, and wherein said polymer composition is water swellable and water insoluble at 25° C. and degradable to a water soluble non-crosslinked polysaccharide in an essentially neutral aqueous medium at a temperature of at least 37° C., said process comprising:

(a) forming a water-in-oil dispersion comprising (1) an aqueous alkaline solution of a water-soluble polysaccharide, said aqueous alkaline solution having been rendered basic to a pH of at least 13, through addition of a base, and (2) a water immiscible organic liquid, wherein said aqueous solution is a disperse aqueous phase and said organic liquid is a continuous oil phase of said dispersion;

(b) treating the dispersion with a cyanogen halide wherein said polysaccharide is treated with substantially equimolar quantities of said cyanogen halide and said base; and (c) recovering microparticles of said hydrolytically degradable polymer composition.

11. A process according to claim 10 wherein said cyanogen halide is cyanogen bromide.

12. A process according to claim 10 wherein said aqueous alkaline solution is made alkaline with a strong base and wherein said polysaccharide is treated with substantially equimolar quantities of said cyanogen halide and said strong base.

13. A process according to claim 10 wherein the quantity of said cyanogen halide is from about 0.01 to about 0.25 moles per mole of polysaccharide hydroxyl groups.

14. A process according to claim 13 wherein the quantity of said cyanogen halide is from about 0.02 to about 0.1 mole per mole of polysaccharide hydroxyl groups.

15. A process according to claim 10 wherein said polysaccharide is dextran.

16. A process according to claim 10 wherein microspheres of said crosslinked polymer in hydrated form are formed in the aqueous phase of said dispersion upon treatment of said dispersion with said cyanogen halide.

17. A process according to claim 16 wherein said microspheres of crosslinked polymer in hydrated form are acidified and then neutralized.

18. A process according to claim 17 wherein said microspheres are acidified to a pH of about 2 to about 3.

19. A process according to claim 17 wherein said acidified and neutralized microspheres are dried and recovered, said microspheres as recovered having a particle size predominantly in the range of about 1 to about 100 microns.

20. A process according to claim 19 wherein the microspheres as recovered have a particle size predominantly in the range of about 2 to about 50 microns.

21. A process for preparing a water swellable and hydrolytically labile crosslinked polymer composition in the form of microspheres, wherein said polymer composition is a derivatized dextran comprising (1) dextran chains, (2) crosslinking groups selected from the group consisting of linear imidocarbonate groups, linear carbonate groups and mixtures thereof and is essentially from other crosslinking groups, and (3) a derivative group which is different from and in addition to any groups introduced by treatment with cyanogen halide, said polymer composition being water swellable and water insoluble at 25° C. and degradable to a water soluble non-crosslinked polysaccharide in an essentially neutral aqueous medium at a temperature of at least 37° C., said process comprising:

(a) reacting a water soluble non-crosslinked dextran with a derivative-forming reagent which is capable of reacting with hydroxyl groups of said dextran;

(b) forming a water in oil dispersion comprising an aqueous alkaline solution of dextran, said aqueous alkaline solution having been rendered basic to a pH of at least 13, through addition of a base, and a water immiscible organic liquid, wherein said aqueous solution is a dispersed aqueous phase and said organic liquid is a continuous oil phase of said dispersion;

(c) treating the dispersion with a cyanogen halide wherein said polysaccharide is treated with substantially equimolar quantities of said cyanogen halide and said base;

(d) recovering microparticles of said hydrolytically labile polymer composition.

22. A wound dressing comprising:

(a) a blend of a minor amount of a water swellable and hydrolytically labile polymer composition in the form of microspheres as claimed in claim 1, and a major amount of an amorphous hydrophobic adhesive matrix material, and (b) a waterproof backing sheet;

said blend of said microspheres and said matrix material being applied to one surface of said backing sheet.

23. A wound dressing according to claim 22 wherein said microspheres have particle diameters predominantly in the range of about 1 micron to about 100 microns.

24. A wound dressing according to claim 23 wherein said microspheres have particle diameters predominantly in the range from about 2 to about 50 microns.

25. A wound dressing according to claim 22 wherein said polysaccharide is dextran.

26. A wound dressing according to claim 23 wherein said microspheres are prepared by a process which includes treating a water soluble non-crosslinked dextran with cyanogen bromide and an alkali metal hydroxide in a water-in-oil dispersion comprising an aqueous alkaline solution of said dextran and a water immiscible organic liquid, wherein said solution is a disperse aqueous phase and said organic liquid is a continuous oil phase of said dispersion, and recovering said microspheres.

* * * * *